(12) United States Patent
Karlin et al.

(10) Patent No.: US 11,532,396 B2
(45) Date of Patent: Dec. 20, 2022

(54) SYSTEM AND METHOD FOR PATIENT MONITORING OF GASTROINTESTINAL FUNCTION USING AUTOMATED STOOL CLASSIFICATIONS

(71) Applicant: HealthMode, Inc., San Francisco, CA (US)

(72) Inventors: Daniel R Karlin, New York, NY (US); Peter Dubec, Bratislava (SK); Martin Majernik, Bratislava (SK); Vladimir Boza, Bratislava (SK); Lucia Kvapilova, Nova Ves nad Zitavou (SK); Dana Rajtarova, Bratislava (SK)

(73) Assignee: Mind Medicine, Inc., New York, NY (US)

(*) Notice: Subject to any disclaimer, the term of this patent is extended or adjusted under 35 U.S.C. 154(b) by 287 days.

(21) Appl. No.: 16/899,870

(22) Filed: Jun. 12, 2020

(65) Prior Publication Data
US 2020/0395124 A1 Dec. 17, 2020

Related U.S. Application Data

(60) Provisional application No. 62/860,656, filed on Jun. 12, 2019.

(51) Int. Cl.
*G16H 50/20* (2018.01)
*A61B 5/00* (2006.01)
*G06T 7/00* (2017.01)

(52) U.S. Cl.
CPC .............. *G16H 50/20* (2018.01); *A61B 5/42* (2013.01); *A61B 5/7264* (2013.01);
(Continued)

(58) Field of Classification Search
CPC .......... G16H 50/20; G16H 30/40; A61B 5/42; A61B 5/7264; A61B 5/4255;
(Continued)

(56) References Cited

U.S. PATENT DOCUMENTS

| | | |
|---|---|---|
| 6,571,003 B1 | 5/2003 | Hillebrand et al. |
| 6,619,961 B2 | 9/2003 | Baird et al. |

(Continued)

FOREIGN PATENT DOCUMENTS

| | | |
|---|---|---|
| CN | 104410654 A | 3/2015 |
| CN | 105654469 B | 6/2016 |

(Continued)

*Primary Examiner* — Chuong A Ngo
(74) *Attorney, Agent, or Firm* — Kohn & Associates, PLLC

(57) ABSTRACT

A method of data collection of stool data via a mobile device operable to enable monitoring of gastrointestinal function. A related method of long-term monitoring of patient gastrointestinal function, using one or more signal processing tools (e.g. machine learning algorithms) for automatically interpreting patient stool data, including real-time patient-assessments, in order to detect an adverse clinical event from patient stool data. A system for facilitating real-time monitoring the gastrointestinal function, the system comprising: a camera on a mobile device, a user interface that facilitates self-monitoring of stool characteristics, so as to create health-monitoring data; mobile device storage, server storage, and remote storage (with at least one communication link between them) for storing some or all of the health-monitoring data; and a processor for interpreting such health-monitoring data for clinical or other health-monitoring application.

24 Claims, 23 Drawing Sheets

(52) U.S. Cl.
CPC .. *G06T 7/0012* (2013.01); *G06T 2207/10024* (2013.01); *G06T 2207/20081* (2013.01); *G06T 2207/20084* (2013.01); *G06T 2207/30092* (2013.01)

(58) Field of Classification Search
CPC ......... G06T 7/0012; G06T 2207/10024; G06T 2207/20081; G06T 2207/20084; G06T 2207/30092; G06T 2200/24
See application file for complete search history.

(56) References Cited

U.S. PATENT DOCUMENTS

| | | |
|---|---|---|
| 9,927,410 B2 | 3/2018 | Carney et al. |
| 2007/0224584 A1 | 9/2007 | Hokanson |
| 2009/0232409 A1* | 9/2009 | Marchesotti .......... G06T 7/0002 |
| | | 382/254 |
| 2010/0135907 A1 | 6/2010 | Cranley et al. |
| 2013/0052624 A1 | 2/2013 | Saps et al. |
| 2015/0206151 A1 | 7/2015 | Carney et al. |
| 2017/0039337 A1 | 2/2017 | Neuhauser et al. |
| 2017/0340306 A1 | 11/2017 | Spiegel et al. |
| 2018/0271501 A1 | 9/2018 | Wang |
| 2021/0265059 A1* | 8/2021 | Paineau ................. G16H 50/20 |

FOREIGN PATENT DOCUMENTS

| | | |
|---|---|---|
| KR | 101368144 B1 | 2/2014 |
| KR | 101595434 B1 | 2/2016 |
| WO | 2018035147 A1 | 2/2018 |

\* cited by examiner

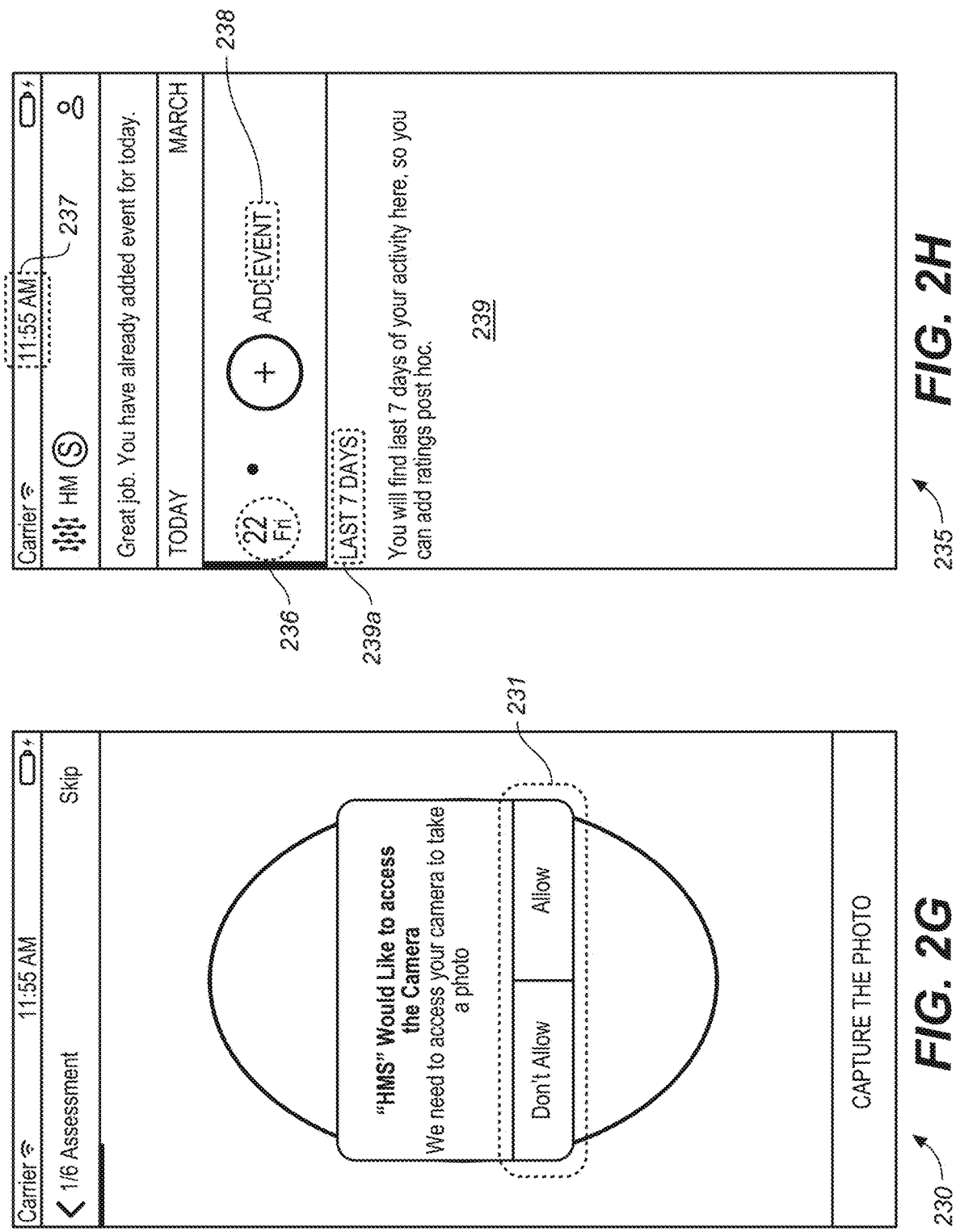

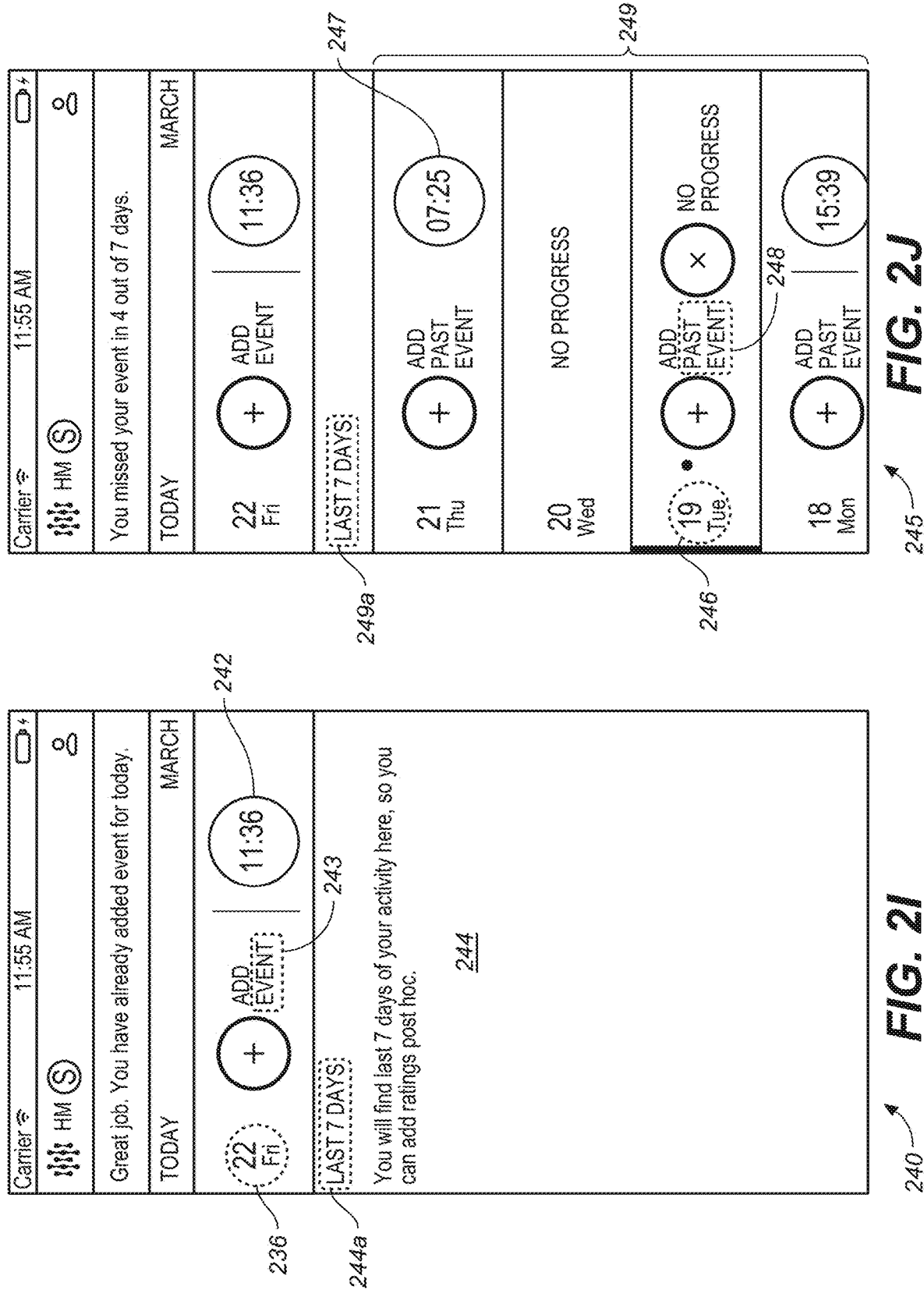

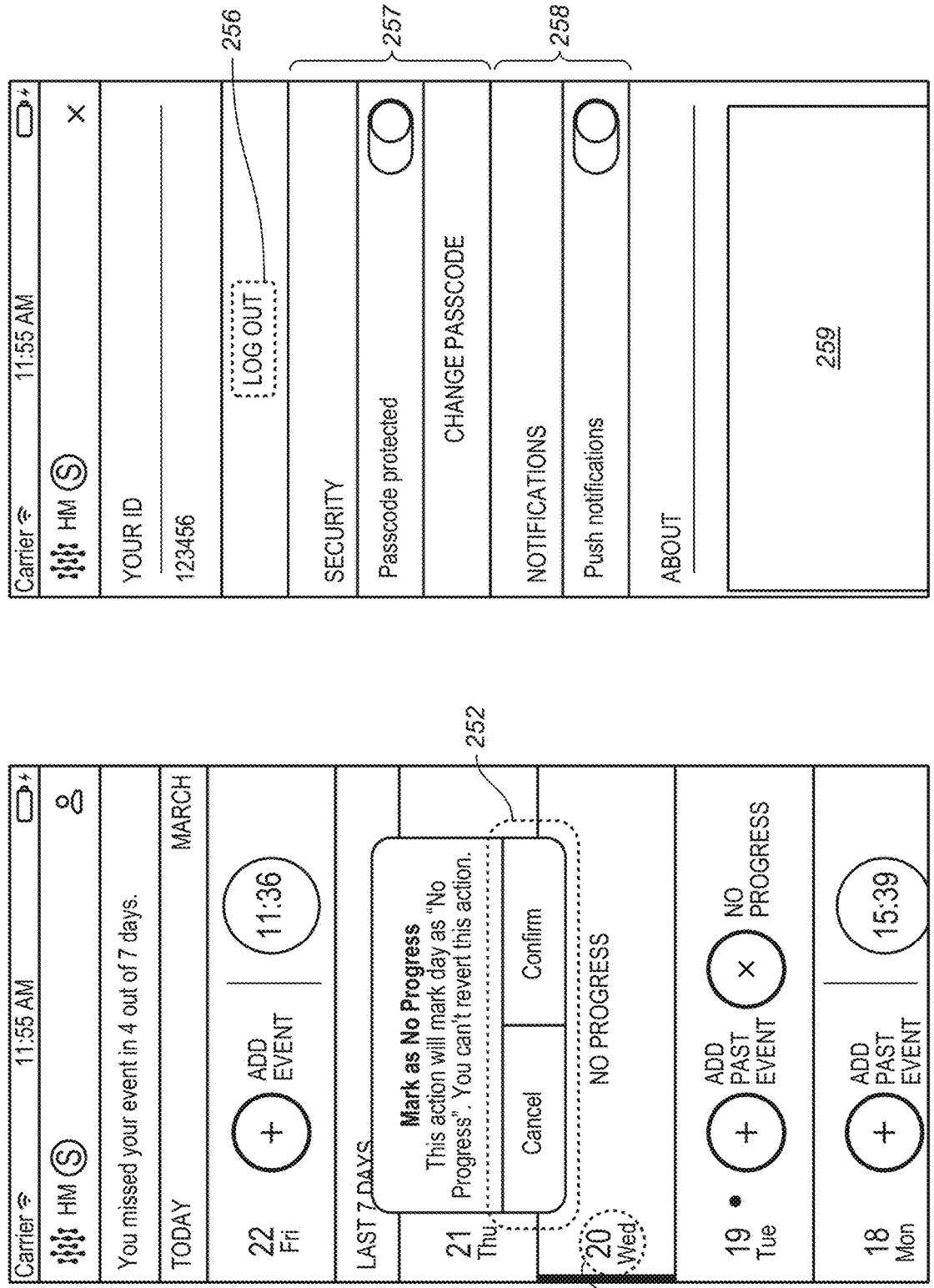

FIG. 2M

- 261: Set your password
- 262: (keypad)
- 260

FIG. 2N

- 271: Please specify time of the event
- 22.March 2019
- 8, 9, 10, 11, 12, 1, 2
- 33, 34, 35, 36, 37, 38, 39
- AM / PM
- 267
- START THE ASSESSMENT
- 265

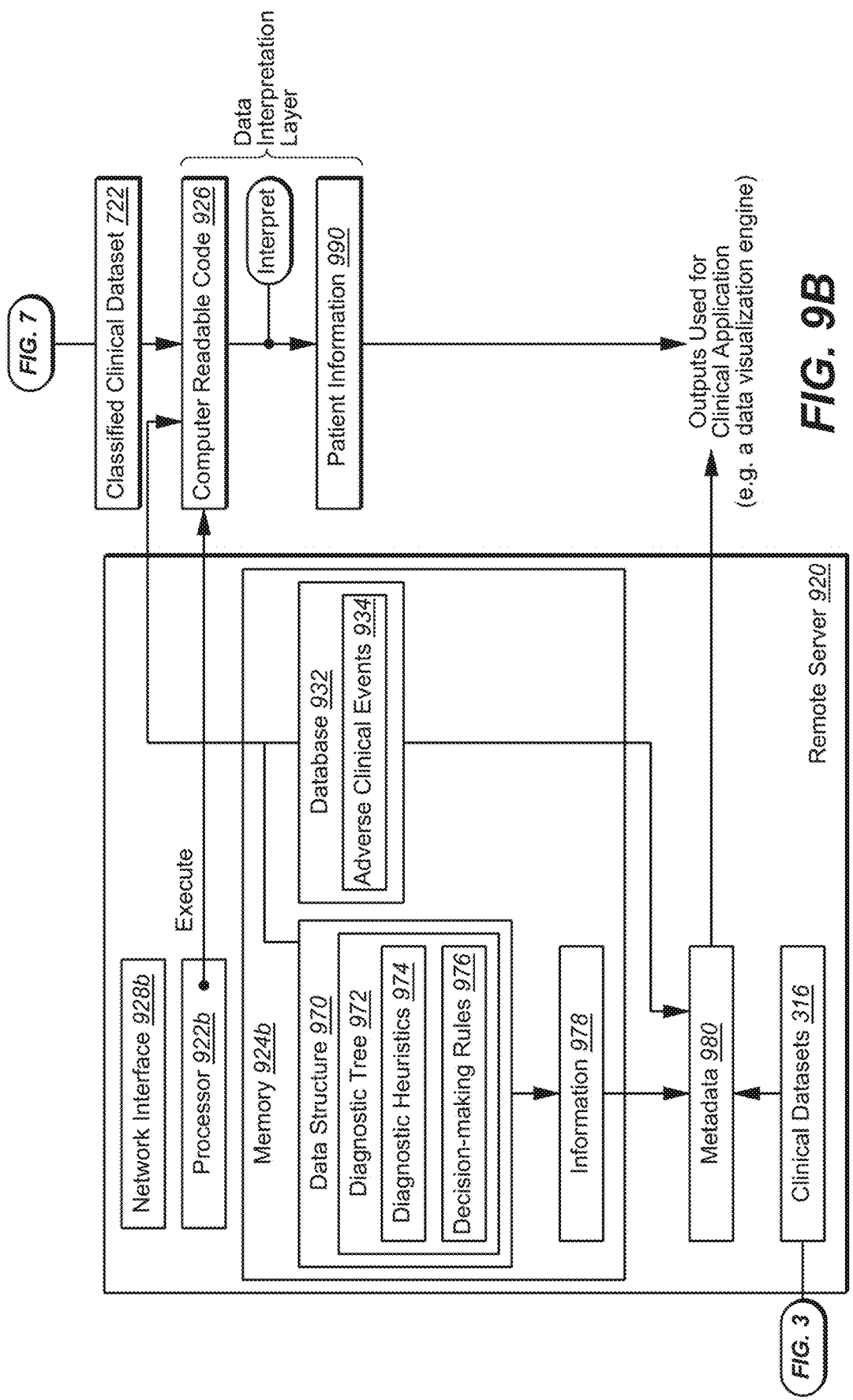

SYSTEM AND METHOD FOR PATIENT MONITORING OF GASTROINTESTINAL FUNCTION USING AUTOMATED STOOL CLASSIFICATIONS

CROSS-REFERENCE TO RELATED APPLICATIONS

This application claims the benefit of U.S. Provisional Patent Application No. 62/860,656 titled "System and Method for Patient Monitoring of Gastrointestinal Function Using Automated Stool Classifications," filed Jun. 12, 2019, which is hereby incorporated herein by reference in its entirety for all purposes.

BACKGROUND

In clinical trials and continuous therapy, clinicians are often unable to objectively assess therapy progression and estimate prognosis for patients, due to a lack of continuous representative data collection. In-hospital or in-clinic assessments are too few and out of context of the patient's day-to-day activities, while suffering from random sampling issues that may mask change over time. Indicators of a patient's progress under therapy may not be collected on a continuous basis, and clinicians may also lack understanding of potential causal relationships (e.g. between fatigue and physical activity, event-triggered tremors, or between physical activity and degradation of upper limb movement). A lack of continuous status indicators for a patient under therapy can lead to inappropriate decision making with respect to healthcare seeking behaviors.

SUMMARY

The systems and methods described herein pertain to patient stool (fecal) and gastrointestinal health monitoring, and in particular, improving patient compliance with clinical protocols. The systems and methods use automated classifications of patient stool (fecal) and gastrointestinal data, and in particular, automated Bristol Stool Chart classifications. Patient stool (fecal) images (for example, video and video frames) are processed using a camera on mobile device (also referred to herein as "mobile computing device"). Long-term monitoring of patient gastrointestinal function uses such images of patient stool in conjunction with signal processing tools, such as machine learning methods, for classifying patient medical data.

A system of one or more computing devices can be configured to perform particular operations or actions by virtue of having software, firmware, hardware, or a combination of them installed on the system, which in operation causes or cause the system to perform the actions. One or more computer programs can be configured (using, for example, computer-readable code) to perform particular operations or actions by virtue of including instructions that, when executed by data processing apparatus, cause the apparatus to perform the actions.

One general aspect includes a method of data collection of clinically relevant stool data via a mobile device, operable to enable patient monitoring of gastrointestinal function so as to improve patient compliance with clinical protocols. The method includes the steps of: creating a digital image of a stool sample; editing color in the digital image using an automated color-editing (e.g., color-inversion) process, so as to create a color-edited image; creating a set of annotations associated with the digital image, using the color-edited image, a set of stool scale classifications and other information; storing the set of annotations associated with the digital image in a patient database; and uploading the digital image in a remote storage. Other embodiments of this aspect include corresponding computer systems, apparatus, and computer programs (for example, computer-readable code) recorded on one or more computer storage devices, each configured to perform the actions of methods described herein.

Another general aspect includes a method of long-term monitoring of patient gastrointestinal function for clinical application, the method including: obtaining a digital image of a stool sample; classifying the digital image to obtain a classified digital image using at least one signal processing tool, such as a machine learning algorithm. Machine learning algorithms may include, for example: a stool ID from noise model; a stool color classifier model; stool size classifier model; a stool texture classifier model; a stool float classifier model; and a frequency and cadence classifier model. The method of long-term monitoring of patient gastrointestinal function also includes annotating the classified digital image with patient-assessed information, to obtain at least one subjective annotation associated with the classified digital image of the stool sample. Such patient-assessed information may be obtained through various means, including but not limited to information obtained directly from the patient and/or the patient's caregiver. The method of long-term monitoring of patient gastrointestinal function also includes storing the at least one subjective annotation associated with the classified digital image in a database of patient stool monitoring information. The method of long-term monitoring of patient gastrointestinal function also includes interpreting the database of patient stool monitoring information for clinical application. Other embodiments of this aspect include corresponding computer systems, apparatus, and computer programs recorded on one or more computer storage devices, each configured to perform the actions of methods described herein.

Yet another general aspect includes a system for patient real-time monitoring of gastrointestinal function for clinical application, the system including: a camera on a mobile device for capturing medical image data relating to a patient stool; a medical image data processor configured to create a color-edited image by a color inversion process; a user interface to enable patient annotations associated with the medical image data using the color-edited image; a mobile device storage for storing the patient annotations associated with the medical image data, so as to create one or more sets of clinical data; a server storage for storing a first database including the one or more sets of clinical data; a communication link between the mobile device and the server for uploading the one or more sets of clinical data from the mobile device storage to the server storage; a processor with at least one signal processing tool (such as, for example, a machine learning algorithm) for classifying the one or more sets of clinical data into a classified clinical dataset; a second database for storing the classified clinical dataset; a data structure including a clinical diagnostic tree; a third database for storing a plurality of adverse clinical events; and a processor for interpreting the classified clinical dataset using the clinical diagnostic tree and the third database. Other embodiments of this aspect include corresponding computer systems, apparatus, and computer programs recorded on one or more computer storage devices, each configured to perform the actions of methods described herein.

BRIEF DESCRIPTION OF THE DRAWINGS

FIGS. 9A and 9B are schematics illustrating one aspect of the method and system described herein.

DETAILED DESCRIPTION

Figure 1A:
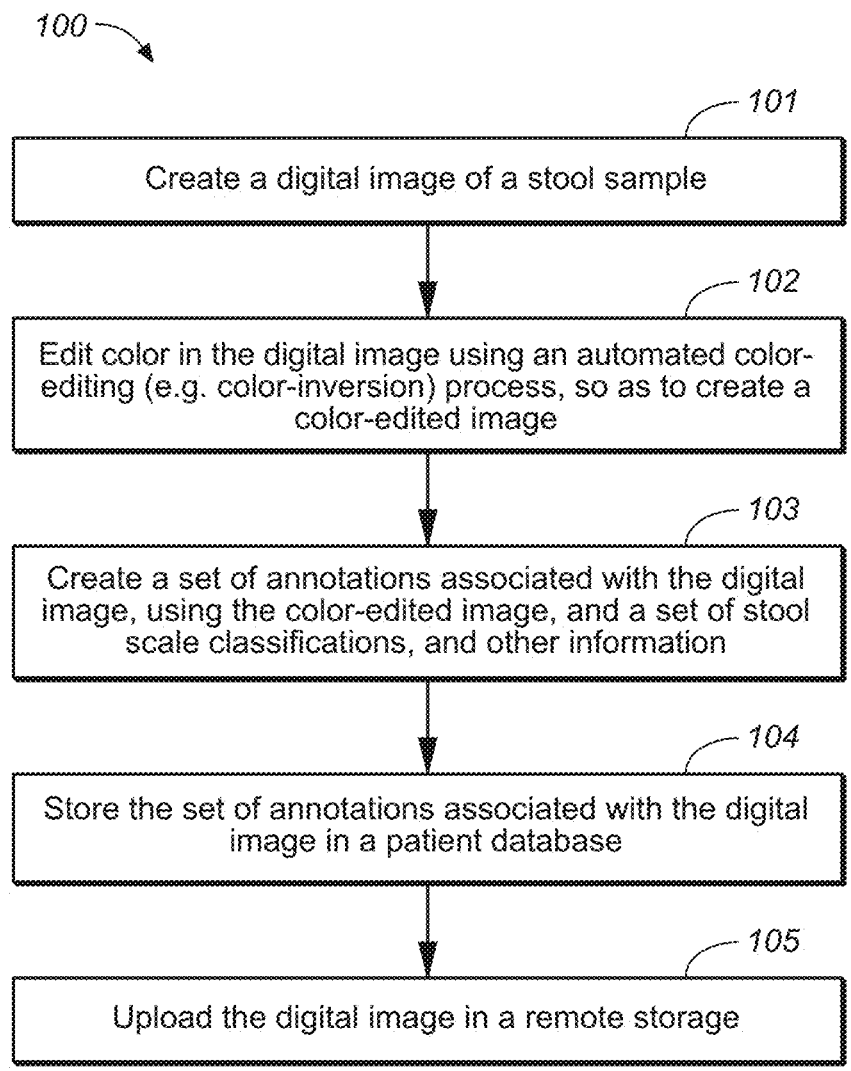
FIGS. 1A and 1B are schematics of a flowchart and a mobile device programmed to perform actions according to one aspect of the method and system described herein.

Development of digital health-monitoring measures enables efficient data collection and virtualization of clinical trials by: (1) decreasing need for site visits in trial pre-screening and recruitment; (2) bringing new possibilities for adaptive design of trials; (3) continuous patient monitoring; (4) measuring intervention efficacy; and (5) clinician monitoring, early detection and prediction analytics for adverse events. The operation of digital measuring is based on the digitization (that is, quantization with respect to level) and coding of a value of a measured physical quantity into a coded signal. (A digital health-monitoring measure may be, for example, a digital endpoint in clinical trials.) The coded signal is fed either to a digital display (in case of digital measuring device) or to a data transmission and processing system (in case of digital measuring transducer). A digital health-monitoring measure is any mechanism for assessing observations, treatment, processes, experience, and/or outcomes of patient care which is operated in digitized form. Here, for example, is described a digitized mechanism of stool assessment and monitoring, which may be used for health-monitoring value, including but not limited to clinical purposes.

Using an automatic method of color editing of a digital image captured by a mobile device camera, and then displaying the color-edited image on the mobile device screen renders patients more compliant with a trial protocol, facilitating real world, long-term data collection and annotation through patient-assessed information, which may be obtained through various means, including but not limited to information obtained directly from the patient and/or the patient's caregiver. For example, an automated color inversion process may be used to obtain such color-edited image. Additionally, an automatic method of transferring collected, unedited digital images by the system enables to keep real life data authentic for analysis.

In one aspect, color-editing is achieved through a process of color inversion. Color inversion of the digital image of a patient's stool serves to offset a cognitive evolutionary mechanism (aversion) by the patient or caregiver when assessing characteristics or properties of the stool. This color-inversion aspect alleviates demand on a patient's time and willingness to assess bowel movement regularly, consistently and exhaustively. In clinical practice, a patient's unwillingness and/or inability to assess bowel movement regularly and consistently may have the unwanted effect of reducing the quality of outcomes of such assessment; it may also introduce systematic errors in monitoring gastrointestinal function.

Patients typically do not comply fully with pre-existing self-assessment protocols requiring close observations of stool; aversion appears to interfere with the required task of stool self-assessment during a passive gastroenterological screening. However, in one aspect of the invention, reversing color of the image of stool (while keeping all other properties, such as, for example, size, shape and consistency constant) is sufficient to offset that aversion. Combining with a convenient adaptable, mobile-based data collection and digitalized annotation tool, color editing, such as color reversal, increases patient compliance with a given self-assessment protocol, thereby facilitating a data collection process that delivers better data quality and quantity. Better and more data, in turn, allow for improved diagnostic, improved prognostic analysis, improved monitoring of disease progression, and improved detection of adverse events.

Thus, one general aspect includes a method of data collection of clinically relevant stool data via a mobile device, for enabling patient monitoring of gastrointestinal function so as to improve patient compliance with clinical protocols. As described below, a system of one or more computers can be configured to perform particular operations or actions by virtue of having software, firmware, hardware, or a combination of them installed on the system which, in operation, causes or cause the system to perform the actions. One or more computer programs can be configured to perform particular operations or actions by virtue of including instructions that, when executed by data processing apparatus, cause the apparatus to perform the actions.

FIG. 1A shows a flowchart for an exemplary method that includes the steps of: creating a digital image of a stool sample (step 101); editing color in the digital image using an automated color-inversion process, so as to create a color-edited image (step 102); creating a set of annotations associated with the digital image in real-time, using the color-edited image and a plurality of stool scale classifications and other information (step 103); storing the set of annotations associated with the digital image in a patient database (step 104); and uploading the digital image in a remote storage (step 105). Other embodiments of this aspect include corresponding computer systems, apparatus, and computer programs recorded on one or more computer storage devices configured to perform the actions of the method.

Figure 1B:
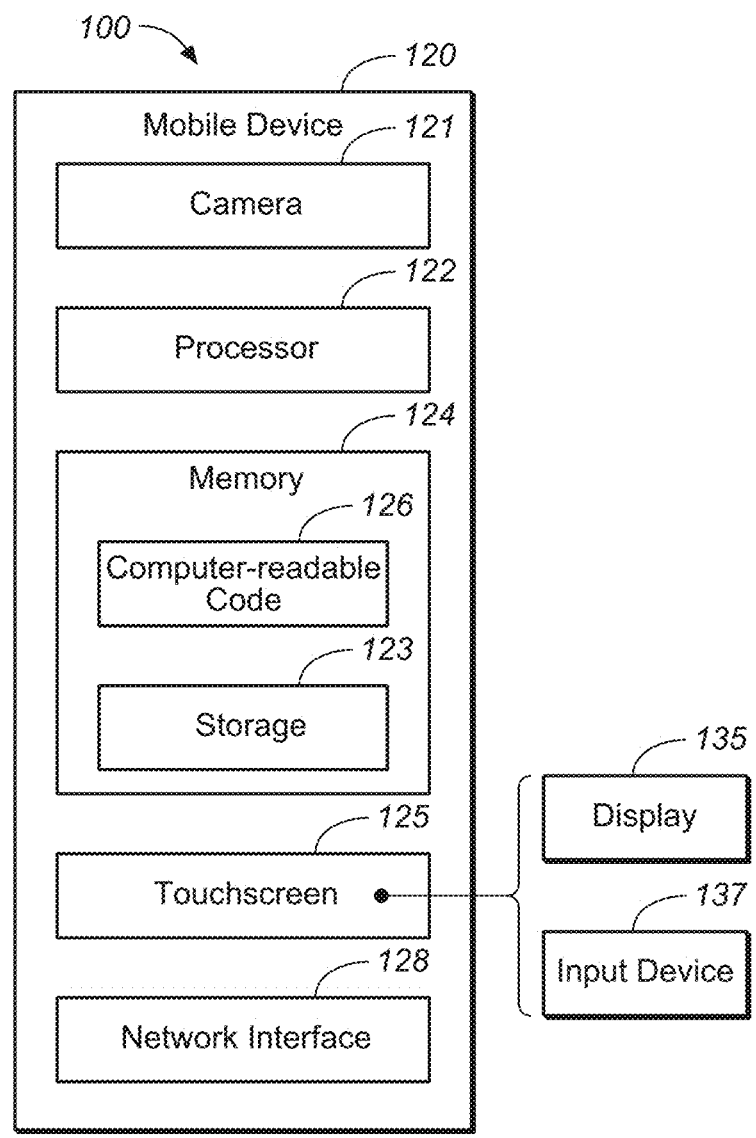

For example, FIG. 1B shows a mobile device 120 (also referred to herein as a "mobile computing device 120"), which may be programmed to perform the actions of the method of FIG. 1A and other methods described herein. In one embodiment, mobile device 120 comprises a camera 121, a processor 122, a memory 124 (which has a storage 123), a touchscreen 125, and a network interface 128. Optionally, the mobile device may have a display 135 that is not a touchscreen, and an input device 137 that is not a touchscreen. For example, input device 137 may be a keypad, a touchscreen, a microphone (which generates an audio feed that may be recorded), or a camera operable to capture still photos and video feed. Mobile device 120 may be any form of mobile computing device, such as, for example (and without limitation), a portable computer, a cellular telephone, a smart phone, a tablet computer, or a portable digital assistant. Network interface 128 is used by mobile device 120 to communicate over a wireless network (not shown), such as a cellular telephone or Wi-Fi network, and then to a remote server (not shown) or over the Internet (not shown). Mobile device 120 is programmable to include computer-readable code 126, which, when executing on processor 122, causes mobile device 120 to perform actions of the methods described herein. The computer-readable code 126 may include portions of code obtained over network interface 128.

In one aspect, and as described in further detail below, the Bristol Stool Chart/Bristol Stool Scale (referred to herein "BSS") may be used to create a set of annotations associated with a digital image of a stool sample captured in real-time, but other stool scale classifications may be used. For a description of BSS, see e.g. U.S. patent application Ser. No. 13/592,906, Tridimensional Stool Assessment Instrument, Methods, and Uses Thereof, filed Feb. 28, 2013 (abandoned). In this aspect, date and time stamping of a data collection event further enables data to be collected, annotated, and stored in real-time, per event, so that more accurate and therefore improved long-term monitoring (e.g. over months or years, as in longitudinal studies) may be achieved.

Figure 2B:
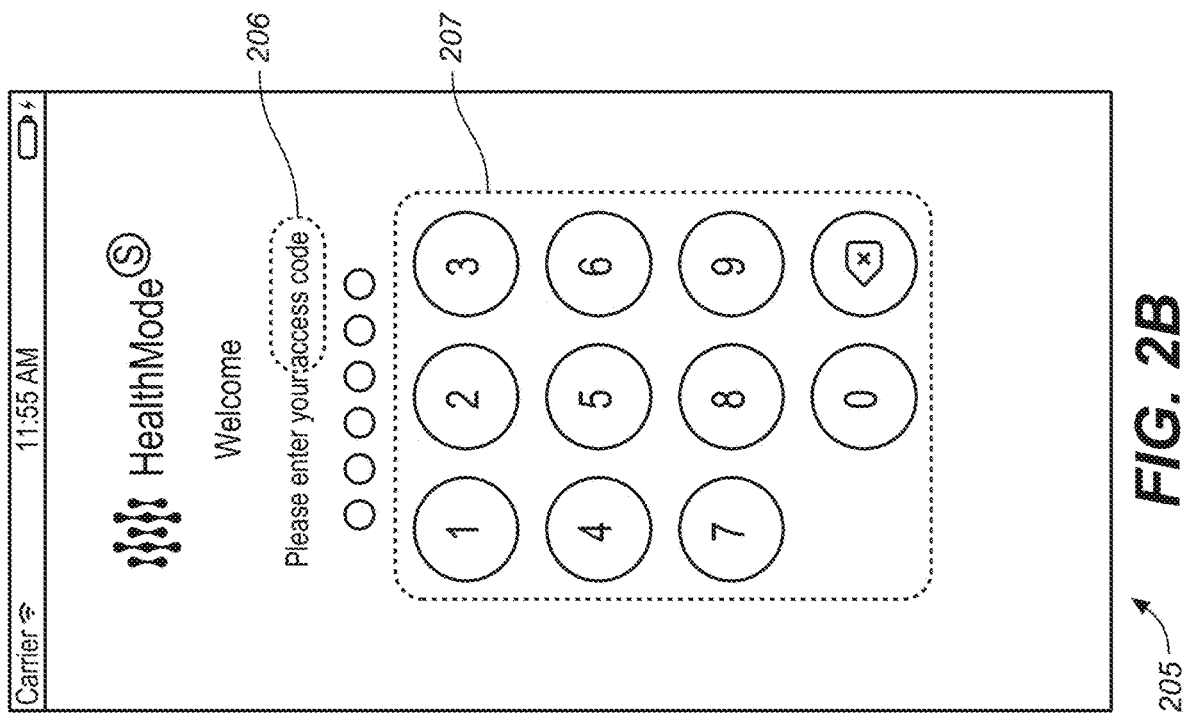
FIGS. 2A through 2N are schematics of screen shots of user interfaces for the mobile device of FIG. 1B, for one aspect of the methods and systems described herein.
FIG. 2O is a schematic drawing for one aspect of method and system described herein.
FIGS. 2P through 2T are schematics of screen shots of user interfaces for the mobile device of FIG. 1B, for one aspect of the method and system described herein.
Figure 2A:
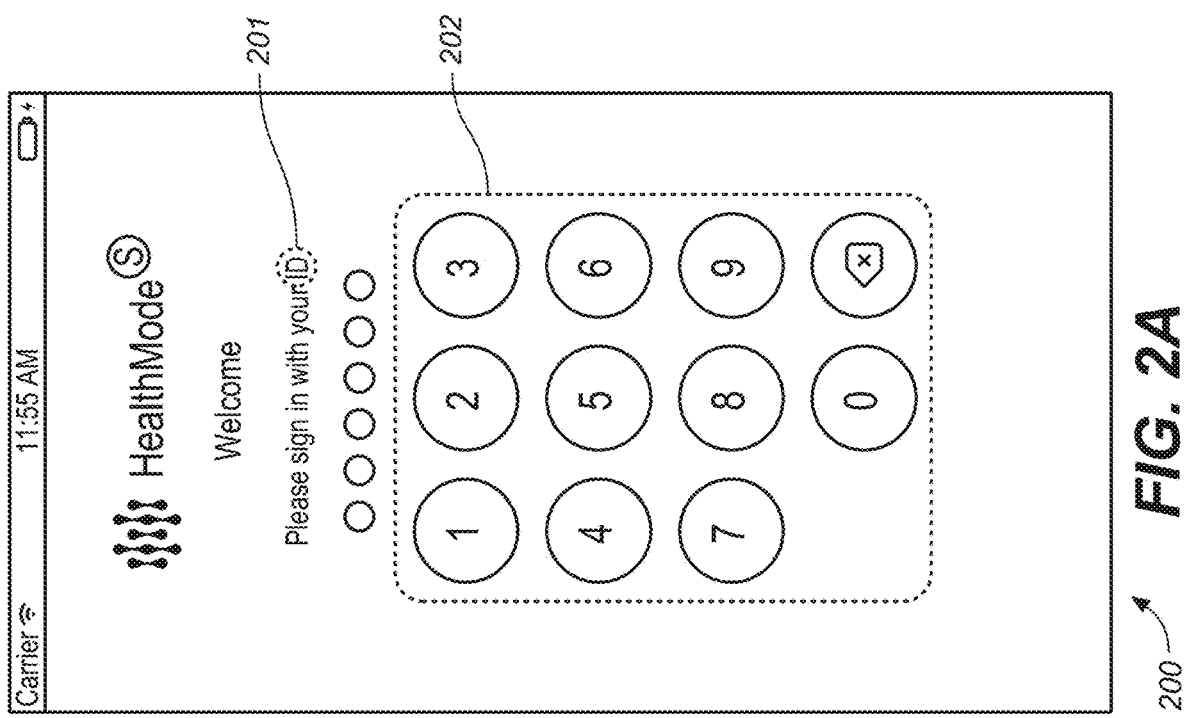
Figure 2D:
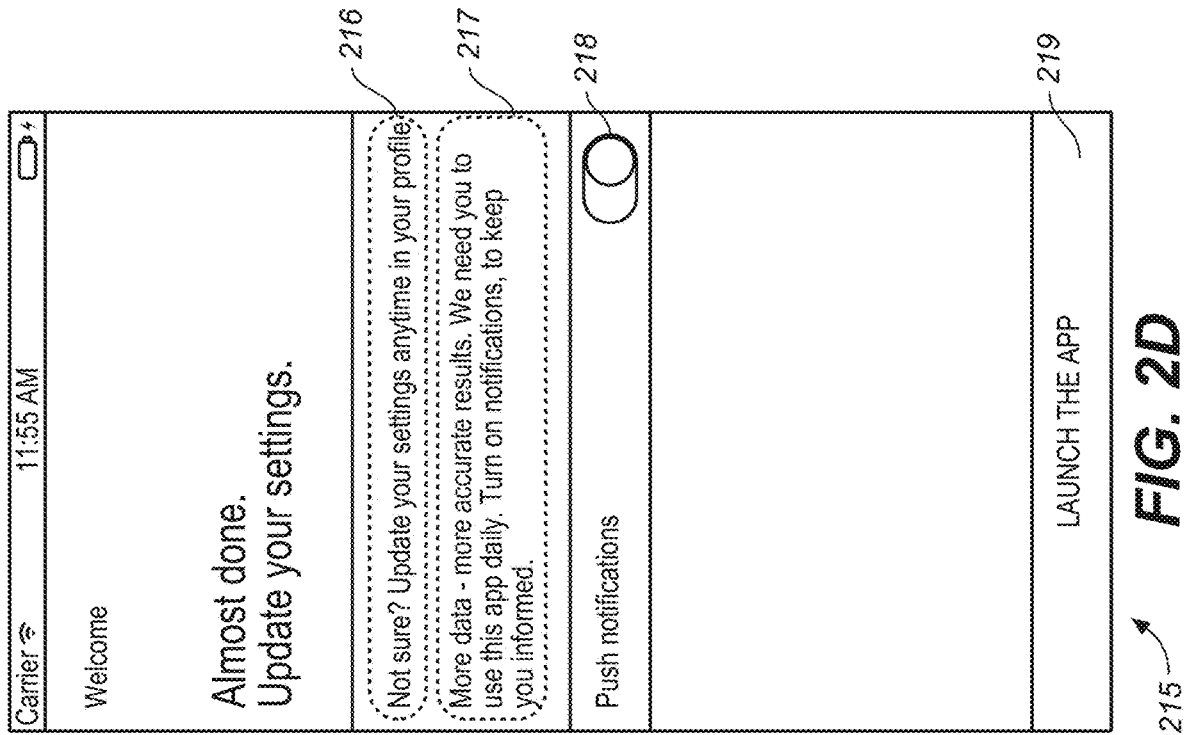
Figure 2C:
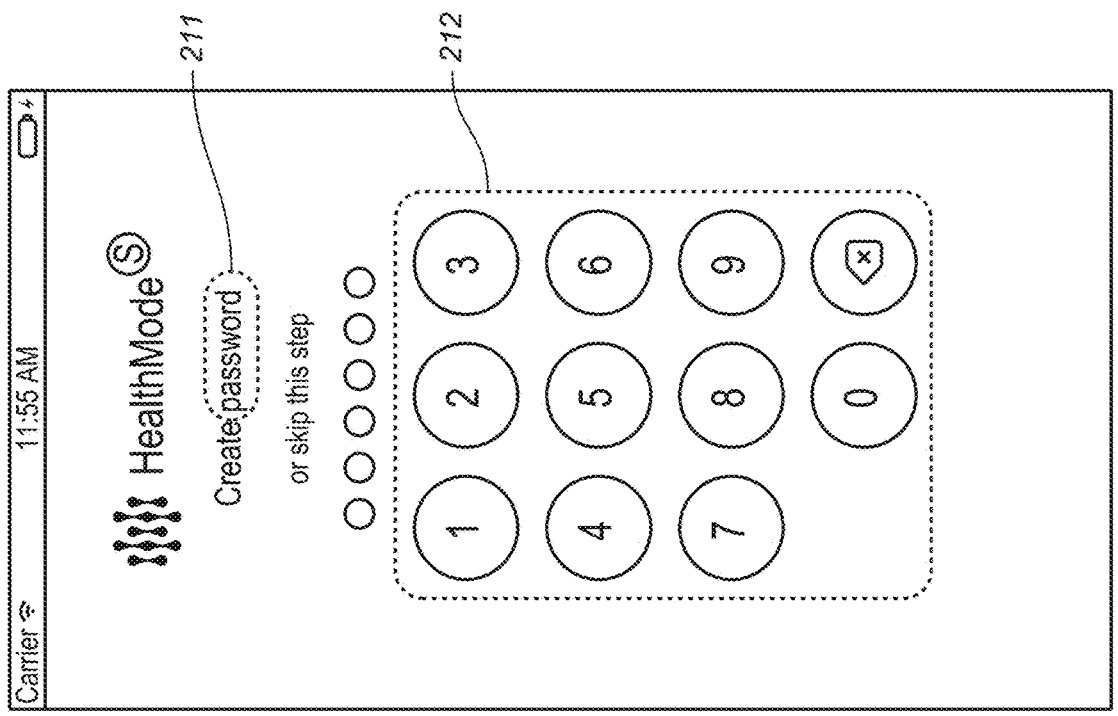
Figures 2E, 2F:
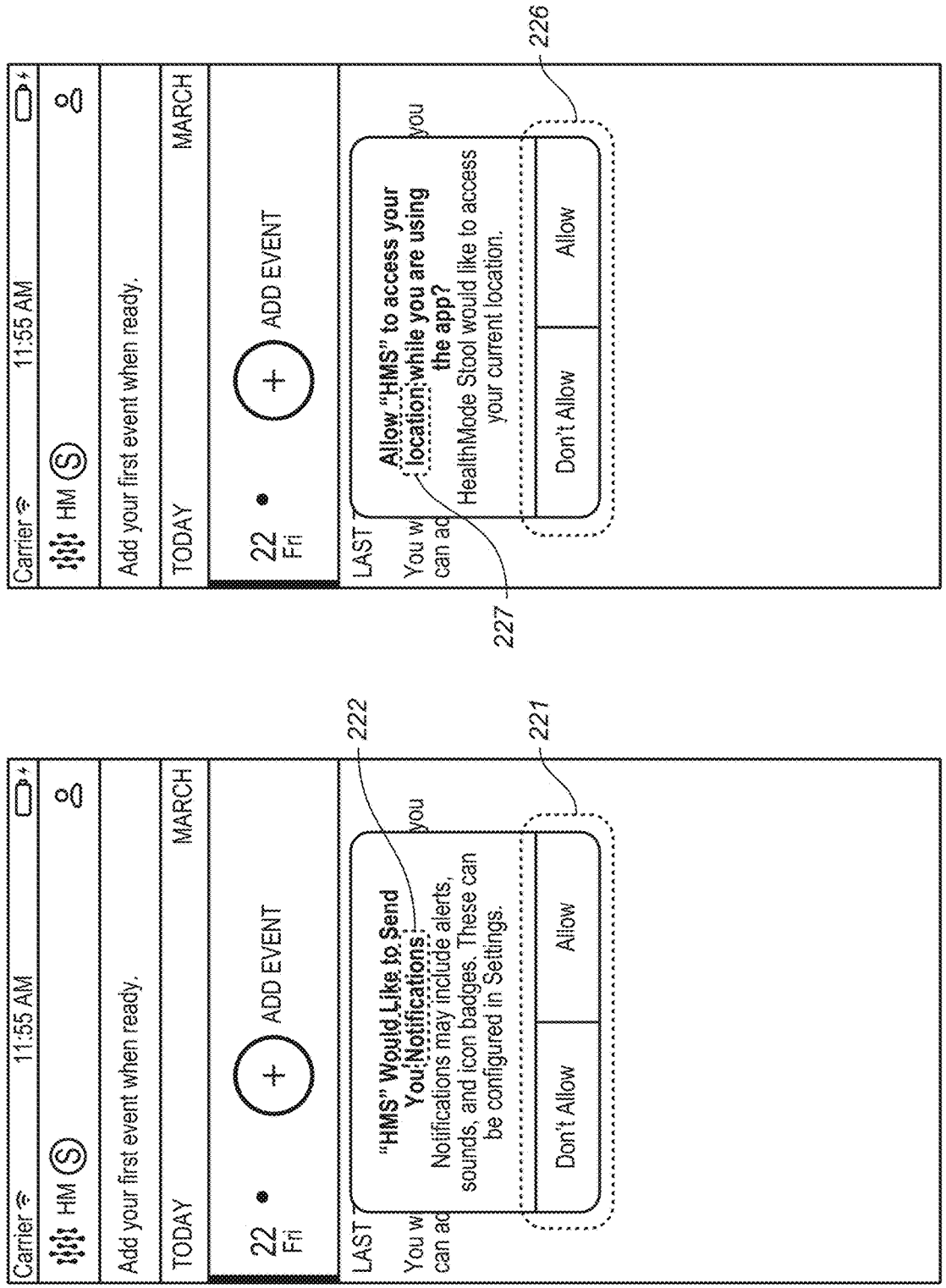
Figure 20:
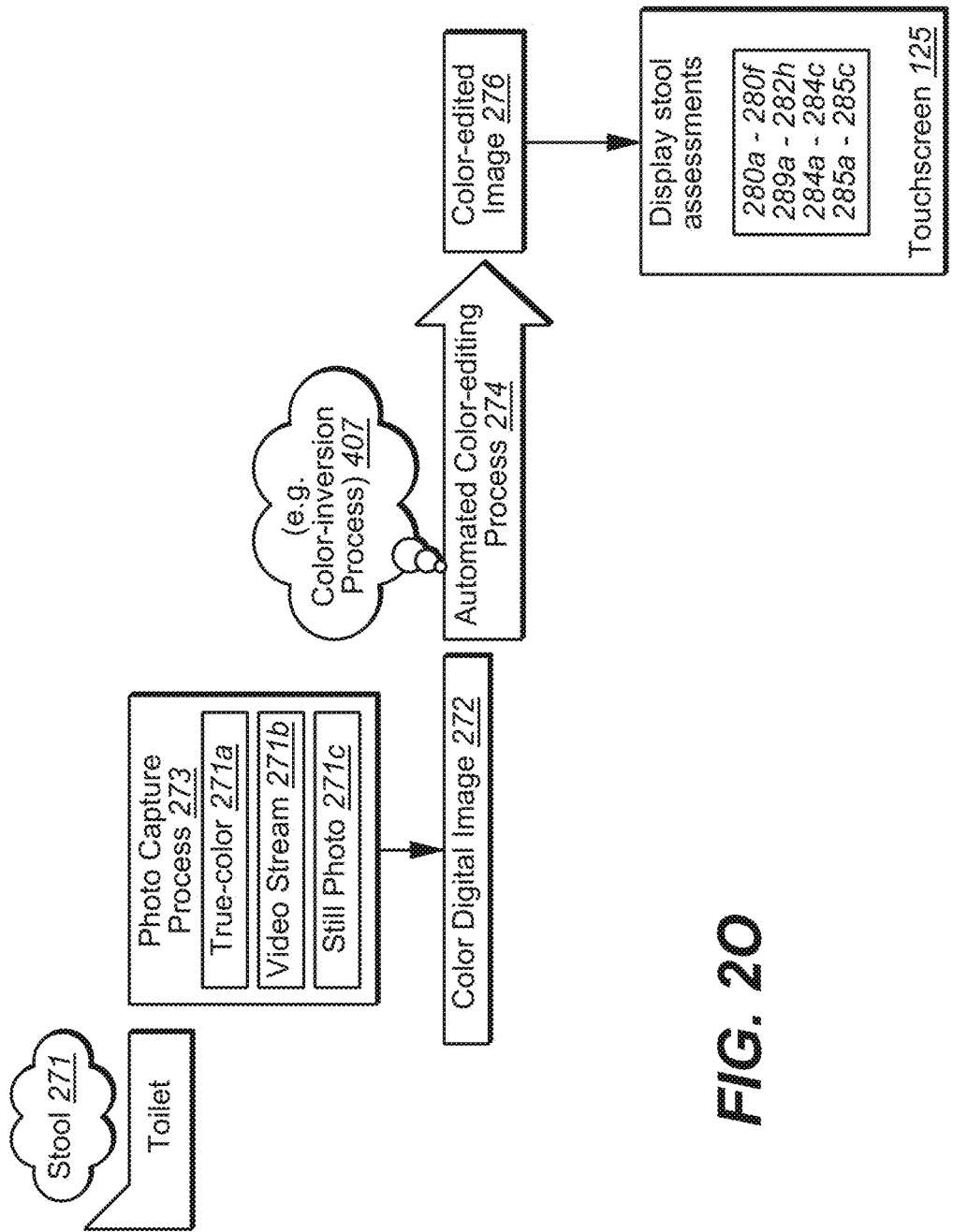
Figure 2P:
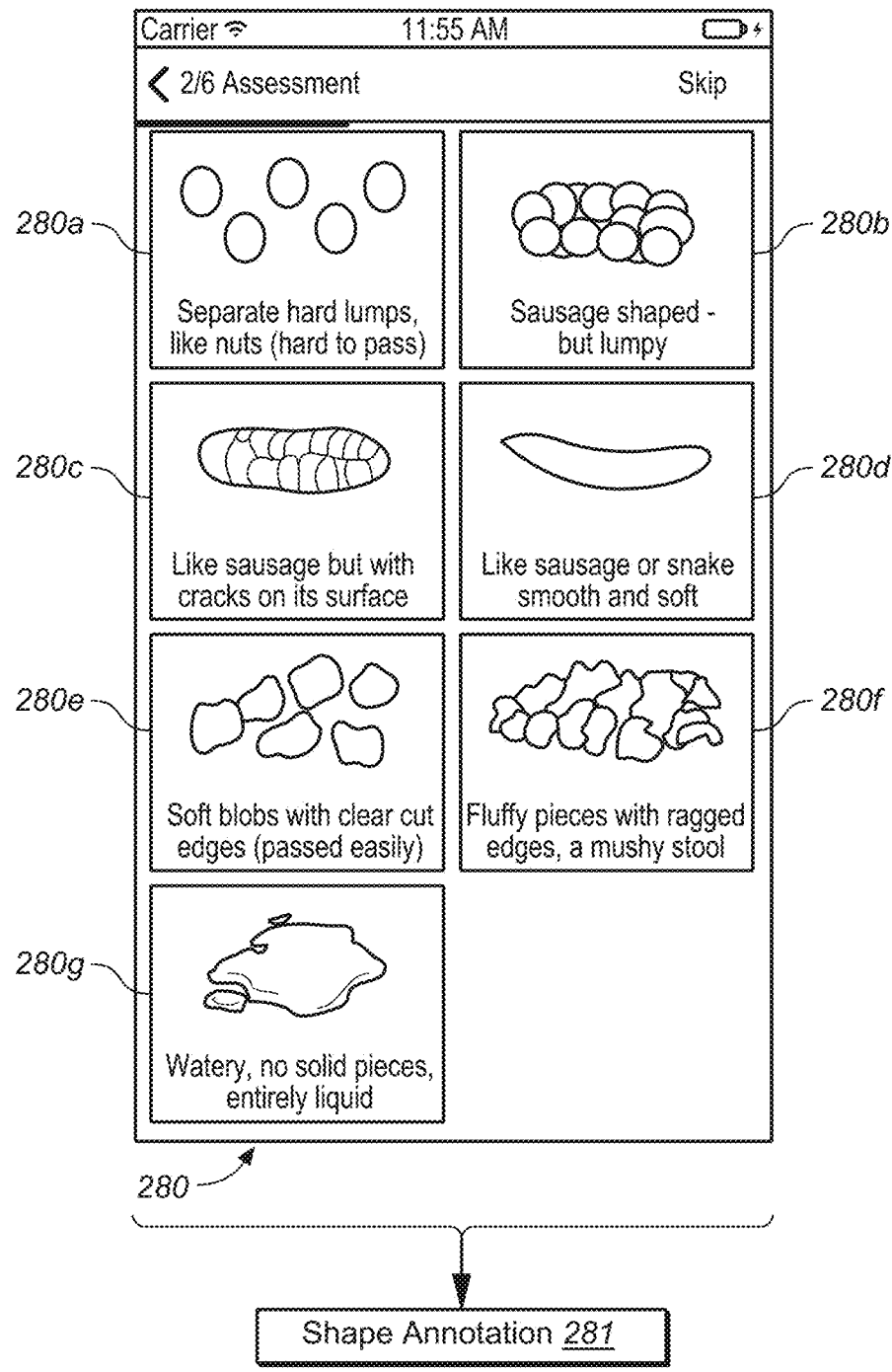
Figure 2Q:
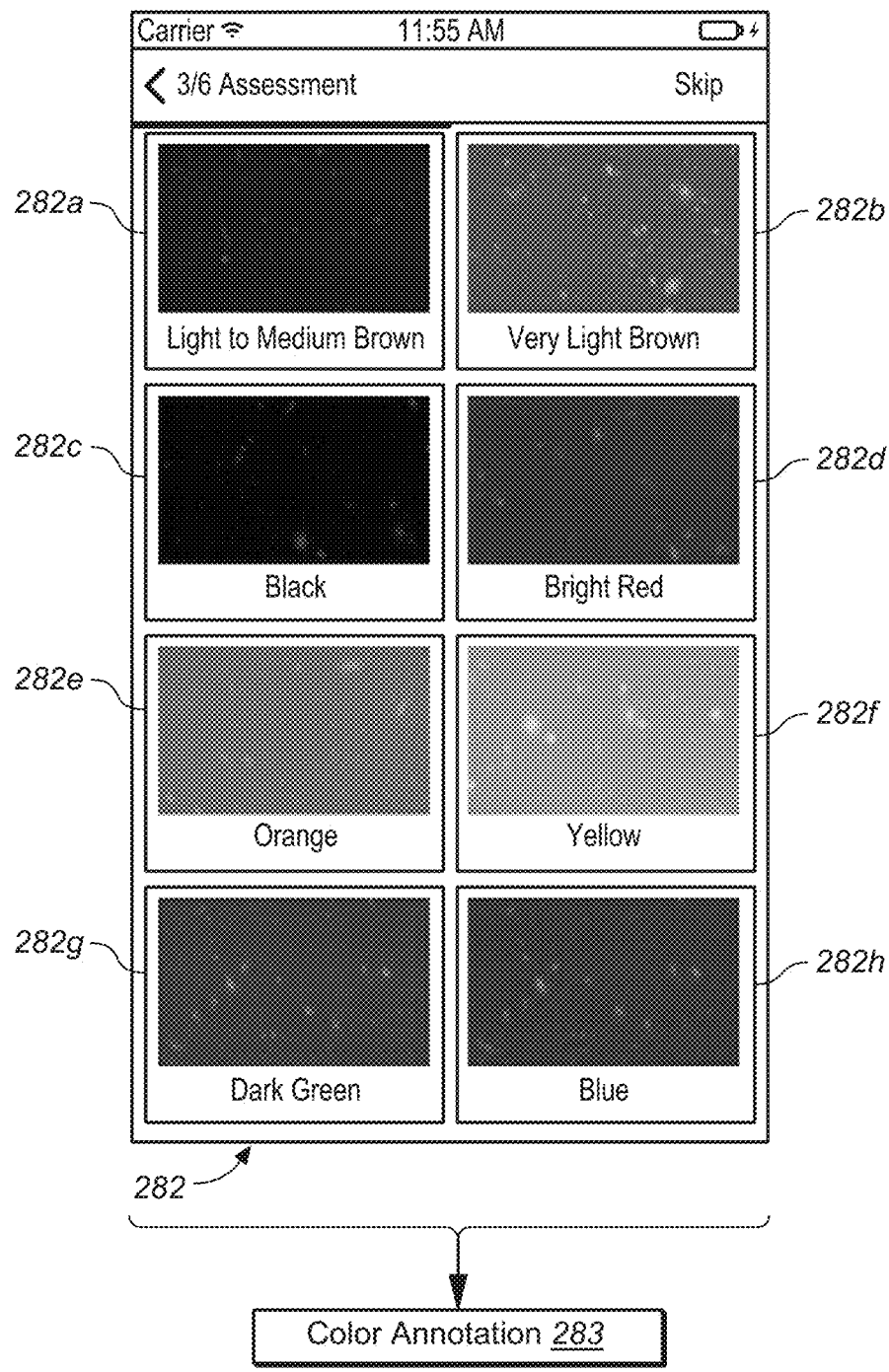
Figure 2R:
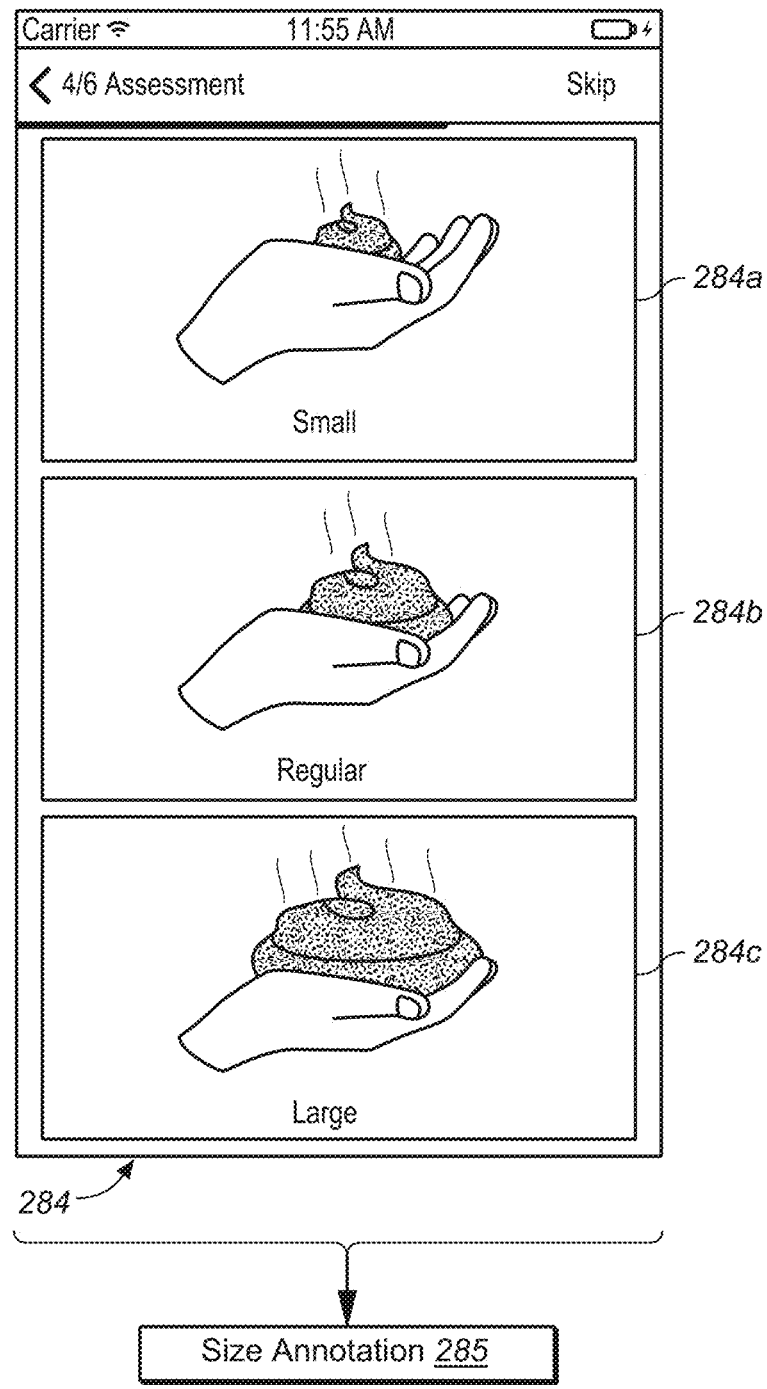
Figure 2S:
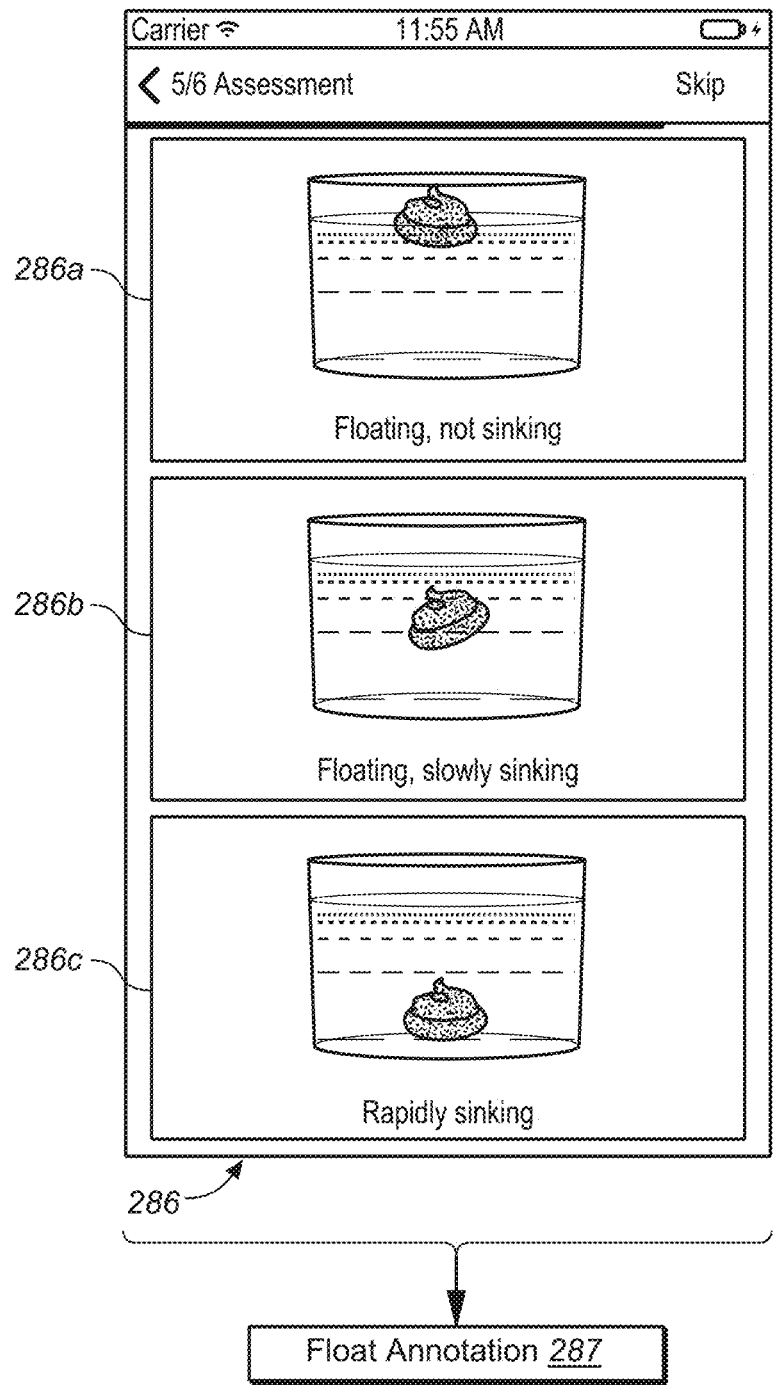
Figure 2T:
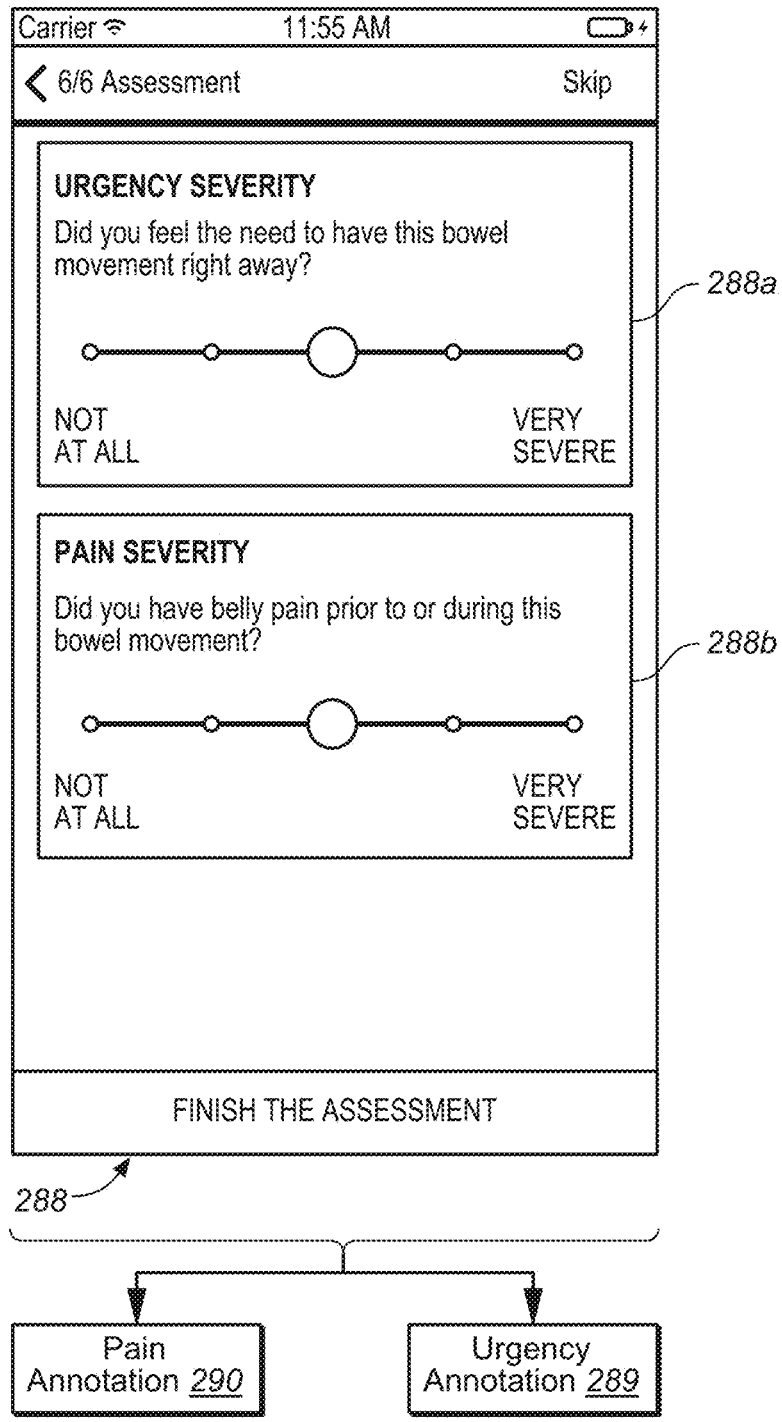

FIGS. 2A-2T show one aspect of mobile device 120 operation during (a) initial setup of the mobile device 120 (see FIGS. 2A-2G), and (b) data collection (digital image capture and annotations) for a stool event (see FIGS. 2H-2T); however, alternative screen aspects may be employed.

In one embodiment, and as exemplified in FIGS. 2A-2T, mobile device 120 is programmed to display a set of user interfaces (listed below) on touchscreen 125, as described below, thereby facilitating data collection of stool sample data:

| User Interfaces | Descriptions |
| --- | --- |
| 200 | A first welcome screen 200 is used for entering an ID 201, which is used to sign in to the system described herein via a touchscreen keypad 202, enabling patient monitoring of gastrointestinal function as described herein. See FIG. 2A |
| 205 | A second welcome screen 205 is used for entering an access code 206, which is used to verify signing into the system described herein via a touchscreen keypad 207, enabling patient monitoring of gastrointestinal function as described herein. See FIG. 2B. |
| 210 | A password creation screen 210 is used for optionally creating a password 211 via mobile device 120, which may also be used to verify signing into the system described herein via a touchscreen keypad 212, enabling patient monitoring of gastrointestinal function as described herein. See FIG. 2C. |
| 215 | An update settings screen 215 is used for (1) enabling updates 216 to one or more user-specified settings, (2) displaying one or more reminders 217, (3) enabling a user to optionally push notifications 218 to mobile device 120, and (4) begin a data collection process 219 ("LAUNCH THE APP"), via touchscreen 125 of mobile device 120, which enables patient monitoring of gastrointestinal function as described herein. See FIG. 2D. |
| 220 | A first permission screen 220 is used to seek permission 221 ("Don't Allow" or "Allow") for the system described herein to send one or more notifications 222 to mobile device 120. See FIG. 2E. |
| 225 | A second permission screen 225 is used to seek permission 226 ("Don't Allow" or "Allow") for the system described herein to have access to a current location 227 of mobile device 120. See FIG. 2F. |
| 230 | A third permission screen 230 is used to seek permission 231 ("Don't Allow" or "OK") for the system described herein to have access to camera 121 of mobile device 120. See FIG. 2G. |
| 235 | A first data collection screen 235 is used to initiate a first recording of a date 236 and a time 237 of a stool event 238, and to provide a summary listing 239 of activities (stool events), stored over a certain time period 239a (for example, over the last seven days) to allow user-entry of past event ratings and/or assessments post hoc (as opposed to real-time) via the touchscreen 125 of mobile device 120. See FIG. 2H. |
| 240 | A second data collection screen 240 is used to initiate one or more subsequent recordings on date 236, and a time 242 of a stool event 243, and to provide a summary listing 244 of activities (stool events), stored over a certain time period 244a (for example, over the last seven days), to allow user-entry of past event ratings and/or assessments post hoc (as opposed to real-time) via touchscreen 125 of mobile device 120. See FIG. 2I. |
| 245 | A third data collection screen 245 is used to initiate one or more subsequent recordings of a past date 246 and/or a past time 247 of a stool event 248, and to provide a summary listing 249 of activities (stool events), stored over a certain time period 249a (for example, over the last seven days), to allow user-entry of past event ratings and/or assessments post hoc (as opposed to real-time) via touchscreen 125 of mobile device 120. See FIG. 2J. |
| 250 | A fourth data collection screen 250 is used to record a date 251 by selecting an indicator 252 ("Cancel" or "Confirm") so as to record absence of a stool event on date 251 ("No Progress"). See FIG. 2K |
| 255 | A fifth data collection screen 255 is used to (1) permit logout 256 of the data collection process 219, (2) permit a change 257 of security settings, permit a change 258 push notification settings, and/or provide other information 259 to a user via touchscreen 125 (or display 135) of mobile device 120. See FIG. 2L. |
| 260 | A password setting screen 260 is used for optionally setting a password 261, which may be used to verify signing into the system described herein via a touchscreen keypad 262, thereby enabling patient monitoring of gastrointestinal function as described herein. See FIG. 2M. |
| 265 | A time setting screen 265 is optionally used for specifying a time 267 of a stool event 271 (not shown). See FIG. 2N. |
| 270 | User interface 270 (not shown) is a first assessment screen that allows for real-time capture of a true-color image 271a of a stool event 271 via camera 121 of mobile device 120. User interface 270 thereby enables a user to create a video stream 271b or a still photo 271c of stool event 271 shortly following elimination. See FIG. 2O. A digital image 272 of a stool sample produced by stool event 271 is created by a photo-capture process 273, which is further described below. Digital image 272 is then input to an automated color-editing process 274, further described below, to create a color-edited image 276 of the stool sample. See FIG. 2O. Color-edited image 276 is presented to the user via touchscreen 125 (or display 135) in connection with user entries of various stool assessments, as described in further detail below. |
| 280 | A second assessment screen 280 is used to obtain user entry of a stool shape assessment selected from a set of proposed shape assessments—280a, 280b, 280c, 280d, 280e, 280f and 280g—which is then used to create a |

-continued

| User Interfaces | Descriptions |
|---|---|
| | shape annotation 281 regarding shape of stool associated with digital image 272. See FIG. 2P. Shape annotation 281 is then stored in mobile device storage 123 of memory 124. |
| 282 | A third assessment screen 282 is used to obtain user entry of a stool color assessment selected from a set of proposed color assessments—282a, 282b, 282c, 282d, 282e, 282f, 282g and 282h—which is then used to create a color annotation 283 regarding color of stool associated with digital image 272. See FIG. 2Q. Color annotation 283 is then stored in mobile device storage 123 of memory 124. |
| 284 | A fourth assessment screen 284 is used to obtain user entry of a stool size assessment selected from a set of proposed size assessments—284a, 284b, and 284c—which is then used to create a size annotation 285 regarding size of stool associated with digital image 272. See FIG. 2R. Size annotation 285 is then stored in mobile device storage 123 of memory 124. |
| 286 | A fifth assessment screen 286 is used to obtain user entry of a stool float assessment selected from a set of proposed float assessments—286a, 286b, and 286c—which is then used to create a float annotation 287 regarding a float property of stool associated with digital image 272. See FIG. 2S. Float annotation 287 is then stored in mobile device storage 123 of memory 124. |
| 288 | A sixth assessment screen 288 is used to obtain user entry of subjective assessments associated with stool event 271-in particular, and as shown in FIG. 2T, a sliding scale of subjective severity assessments for urgency and pain may be used to select from a set of proposed severity scale assessments—288a (urgency) and 288b (pain)—which subjective assessments are then used to create an urgency annotation 289 and a pain annotation 290, respectively, associated with stool event 271 and digital image 272. See FIG. 2T. Urgency annotation 289 and pain annotation 290 are then stored in mobile device storage 123 of memory 124. |

Thus, in the above-described aspect, user interfaces exemplified by 200 (FIG. 2A), 205 (FIG. 2B), 210 (FIG. 2C), 215 (FIG. 2D), 220 (FIG. 2E), 225 (FIG. 2F), 230 (FIG. 2G), 235 (FIG. 2H), 240 (FIG. 2I), 245 (FIG. 2J), 250 (FIG. 2K), 255 (FIG. 2L), 260 (FIG. 2M), 265 (FIG. 2N), 280 (FIG. 2P), 282 (FIG. 2Q), 284 (FIG. 2R), 286 (FIG. 2S), and 288 (FIG. 2T)—are screens displayed on touchscreen 125 to enable user entry of at least one annotation to medical image data, namely, stool sample images captured by camera 121 of mobile device 120. Referring to FIGS. 2O, 2P, 2Q, 2R, 2S and 2T, annotations for stool shape (281), stool color (283), stool size (285), stool float (287), urgency (289) and pain (290) are created from user assessments using a color-edited image 276, which derives from a digital image 272 of a stool sample via an automated color-editing process 274, an example of which—color inversion—is further described below. The user interfaces shown include implementation of Bristol Stool Chart (BSS) assessments, used to create a set of annotations associated with digital image 272, but other stool scale classifications may be used. Also, the order in which these exemplary user interfaces are displayed to a user is by way of example only, and is not intended to limit the functionality of the system and method described herein.

After collecting preliminary setup information for the mobile device (for example, establishing a password 211 and enabling camera 121; see FIGS. 2A-2N), a digital image 272 of a stool sample is captured (FIG. 2O). The digital image 272 may, for example, be captured as a video frame from a video stream 271b taken by the camera 121, or captured as a still photo 271c taken by camera 121. Automated editing of color in the digital image, using an automated color-editing process 274 (which may be, for example, a color-inversion process 274a) creates a color-edited image 276, which is displayed on the mobile device screen (e.g., touchscreen 125; or display 135). Next, a set of annotations associated with the digital image 272 may be created from stool assessments that may be entered in real-time using the color-edited image 276 and a plurality of stool scale classifications; for example, assessments may relate to shape (280a, 280b, 280c, 280d, 280e, 280f, 280g; FIG. 2P), color (282a, 282b, 282c, 282d, 282e, 282f, 282g, 282h; FIG. Q), size (284a, 284b, 284c; FIG. 2R), and float (286a, 286b, 286c; FIG. 2S), as well as other, more subjective information, such as urgency (288a) and pain (288b) (FIG. 2T). While the figures show use of the BSS method for classifying assessed aspects of the stool sample, other stool scale classifications may be used.

There are multiple options by which digital images of a stool sample may be processed. For example, in one aspect (and as further described below), when a patient or caregiver launches the mobile device camera, a color-inverted layer (also called a "filter") may be added above what the camera processes. The mobile device camera then stores every frame observed in inverted colors in a memory of the mobile device, for subsequent editing (e.g. image annotations and manipulations). When the digital image of the stool is captured, the specific color-inverted frame is matched to a true-color digital image, annotated, and then erased from the memory of the mobile device, once annotations are complete; only the matched true-color digital image is saved and uploaded to one or more servers in the system, as further described below.

Alternatively, in another aspect, both a color-inverted image and the true-color image captured by the camera (e.g. from a video frame) may be saved in a memory of the mobile device, and later, both images may be uploaded to any out-of-device storage (e.g. servers).

Alternatively, in yet another aspect, only one image may be captured and a sequential conversion of color, in any manner specified, may be performed; that is, one aspect of the method utilizes a color-editing feature and only one form of the captured digital image (color-converted or true-color), changing it in steps.

Figure 3:
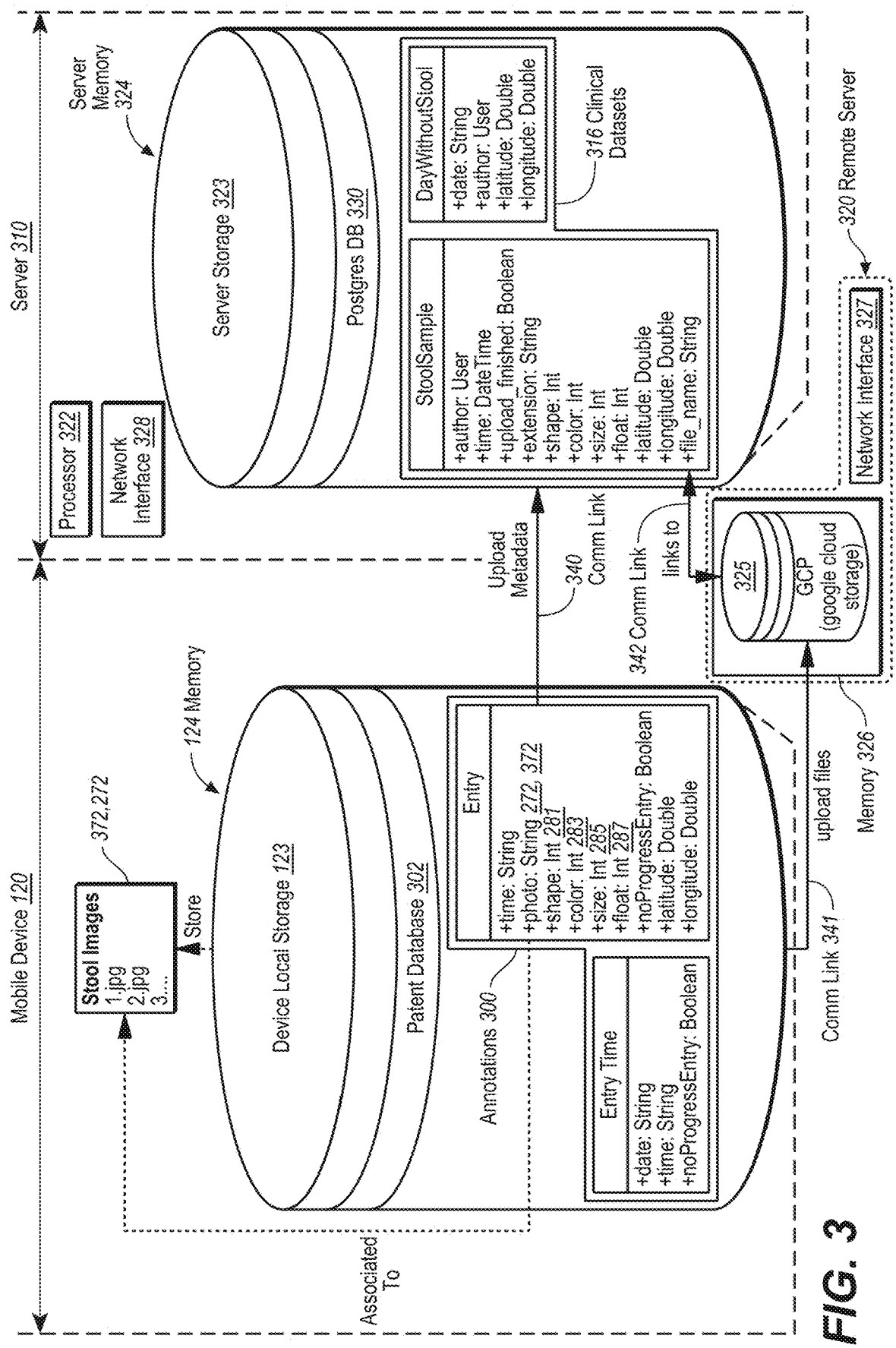
FIG. 3 is a storage architecture diagram for one aspect of the method and system described herein.

FIG. 3 shows one aspect of an exemplary storage architecture for storing a set of annotations 300 associated with the digital image 272 in a patient database 302, and for uploading the digital image 272 in a remote server 320 comprising, for example, cloud storage. As shown in FIG. 3 and elsewhere herein, the use of "GCP" (referring to a "Google Cloud," a third party service) is exchangeable for other similar services, such as, for example, AWS or dedicated servers maintained in-house. The system described herein is not dependent on GCP specifically, and can be migrated/run on other server configurations. Referring to FIG. 3, in this aspect, mobile device memory 124 provides a local storage 123 (i.e. in memory 124 of mobile device 120) operable to store the set of annotations 300 associated with medical image data 372 (i.e., a photo capture of the patient's stool sample), so as to create at least one set of clinical data 316 for a patient. A server 310, includes a processor 322, memory 324, and a network interface 328. Memory 324 stores a database 330 of the at least one set of clinical data 316—namely, patient stool monitoring information. Server 310 facilitates the use of the one or more clinical data sets 316 to be used for clinical applications as described herein. In this aspect, a communication link 340 between mobile device 120 and server 310 is used for uploading the at least one set of clinical data 316 from the local storage 123 to server memory 324 (comprising server storage 323). Additionally, a remote server 320 (e.g., a cloud-based server) may be used for storing and/or processing some or all of the clinical data sets 316, using a remote database 325 housed in a remote server memory 326 (also referred to herein as remote storage device) and a remote server processor (not shown). Remote server 320 also includes a network interface 327, and is enabled to receive uploaded data from mobile device 120 and from server 310 through communication links 341 and 342, respectively. Communication link 341 enables uploading of information and data from local storage 123 (of memory 124) to remote server memory 326; communication link 342 enables both uploading and downloading of information and data between remote server memory 326 and server memory 324. Other embodiments of this aspect include corresponding computer systems, apparatus, and computer programs recorded on one or more computer storage devices, each configured to perform the actions of the methods described.

Figure 4:
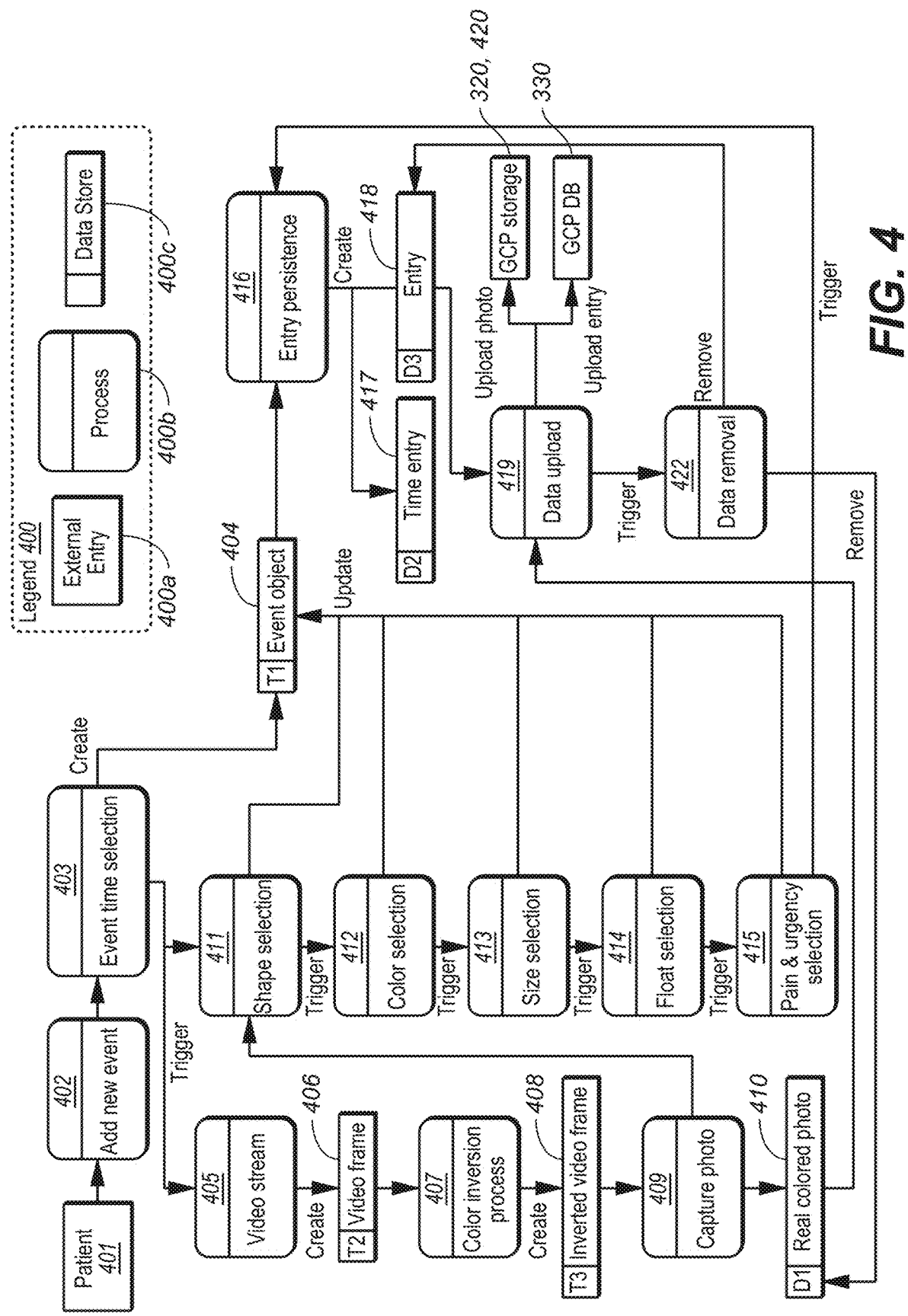
FIG. 4 is an on-device data flow diagram for one aspect of the method and system described herein.

FIG. 4 is an on-device data flow diagram for one aspect of a processing algorithm, implemented in computer-readable code 126 residing in memory 124 of mobile device 120, programmed to execute steps in the method and system described herein. Referring to the LEGEND 400 of FIG. 4: (1) the "External Entity" box shape 400a in the diagram refers to an outside system that sends or receives data, communicating with the system being diagrammed; (2) the "Process" box shape 400b in the diagram refers to any process that changes the data, producing an output; and (3) the "Data Store" box shape 400c in the diagram refers to files or repositories that hold information for later use; in addition, use of a box identifier "I #" represents type of data store (for example D=persisted, T=temporary), where "#" represents a numeric identifier for referencing purposes.

Referring to FIG. 4, in this aspect of the method, the on-device flow diagram may be explained as follows:
1. Patient 401 represents external entity which triggers an initial process, Add New Event process 402.
2. Add New Event process 402 can be perceived as click on button which triggers a next process, Event Time Selection process 403.
3. Event Time Selection process 403 is process during which user specifies time of event. This process creates Event object 404 with specified time attribute. This process also triggers one of two possible next processes Video Stream process 405 or Shape Selection process 411. If delta between selected time and current time is less than 5 minutes, Video Stream process 405 is triggered. Otherwise Shape Selection process 411 is triggered.
4. Event object 404 represents temporary object stored in mobile device memory 124. This object stores attributes of event defined during multiple processes and later is persisted to mobile device memory 124 thanks to process Entry Persistence 416.
5. Video Stream process 405 is a process for capturing a photo. Real-time video stream, representing input to camera 121, is presented on mobile device touchscreen 125 (or display 135) as sequence of one or more Video frames 406.
6. Video frame 406 is a temporary object which represents one frame of video stream. Before presenting on mobile device touchscreen 125 (or display 135), Video frame 406 is transformed using Color Inversion Process 407.
7. Color Inversion Process 407 is the process of applying color inversion filter on Video frame 406 which produces Inverted video frame 408.
8. Inverted video frame 408 is temporary object which represents one frame of video stream in inverted colors.
9. Capture Photo Process 409 is the process of taking a picture which takes a temporary object Video frame 406 and persists it on device as Real colored photo 410. ("Real color" pertains to what is also referred to herein as "true-color.") This process triggers process Shape Selection 411.
10. Real colored photo 410 is persisted jpeg representation of Video frame 406. This object is later uploaded to remote server 320 via Data Upload process 419.
11. Shape Selection 411 is a process of selecting stool shape based on Bristol Stool Scale (BSS). This process updates shape attribute of Event object 404 and triggers process Color Selection 412.
12. Color Selection 412 is a process of selecting stool color based on BSS. This process updates color attribute of Event object 404 and triggers process Size Selection 413.
13. Size Selection 413 is a process of selecting stool size based on BSS. This process updates size attribute of Event object 404 and triggers process Float Selection 414.
14. Float Selection 414 is a process of selecting stool float behavior based on BSS. This process updates float attribute of Event object 404 and triggers process Pain & Urgency Selection 415.
15. Pain & Urgency Selection 415 is a process of specifying pain and urgency severity using two scales with values ranging from 0 (not at all) to 4 (very severe). This process updates pain and urgency attributes of Event object 404 and triggers process Entry Persistence 416.
16. Entry Persistence 416 is a process that takes as input a temporary object, Event object 404, and persists it on mobile device 120 as two representations, Time Entry 417 and Entry 418.
17. Time Entry 417 represents persisted time attribute of newly added event. This object is later presented to a user on a dashboard of a graphical user interface (not shown).
18. Entry 418 represents persisted object containing all attributes of newly added event. This object is later uploaded to a remote server (e.g. server 310 and/or server 320) via Data Upload process 419.
19. Data Upload 419 is a process triggered automatically upon launching the data collection process (219) or by adding a new event. This process takes as input all persisted stool objects (Entry 418) and their corresponding photos, Real colored photo 410, and upload them to remote server 320. Entry 418 is uploaded to DB 325 and/or database 330, and Real colored photo 410 is uploaded to, for example, a remote storage 420, such, as GCP storage 320 and/or server 310. (The system is not dependent on GCP specifically, and can be migrated/run on other server configurations.) This process triggers Data removal process 422.
20. GCP storage 320 is Google cloud storage space represented as external entity. (Other similar storage services may be used, including third party services and/or servers maintained in-house)
21. GCP DB 325 is Google cloud PostgreSQL database represented as external entity. (Other database configurations and/or services may be used).

22. Data removal process 422 is a process of removing data from mobile device 120. After data object Entry 418 and photo Real colored photo 410 is successfully uploaded to a remote server (e.g., 310 and/or 320), they are removed from mobile device 120. Moreover, Time entry 417 objects are filtered and all objects older than 7 days are also removed from mobile device 120 by this process 422.

Other embodiments of this aspect include corresponding devices, processing systems, and computer programs recorded on one or more computer storage devices, each configured to perform the actions of the methods described. The order of selection processes 411, 412, 413, 414 and 415 (and related events) described above is exemplary only.

Figure 5:
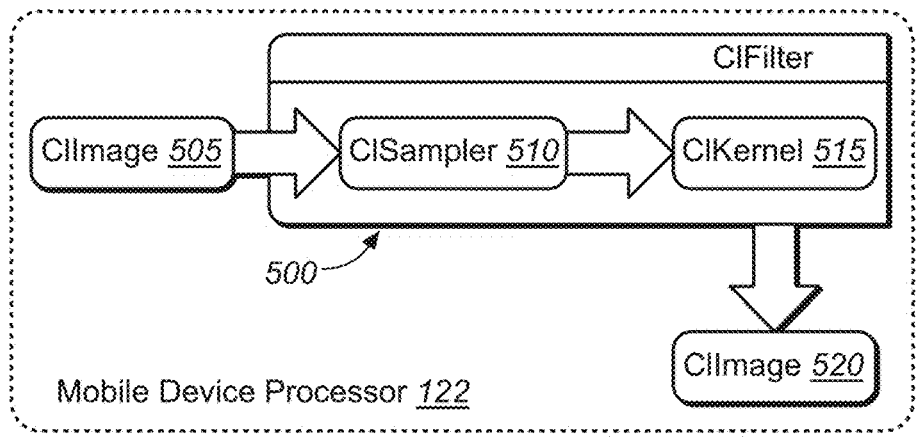
FIG. 5 is a diagram for a color inversion process for one aspect of the method and system described herein.

FIG. 5 is a diagram for a color inversion process performed on processor 122 of mobile device 120 for one aspect of the method and system described herein. In particular, in one aspect, Color Inversion Process 407, depicted in FIG. 4 and described above, includes a process of applying color inversion filter 500 on medical image data 505 (for example, a video frame 406), to obtain a color-edited image 520 (e.g., in the form of an inverted video frame 408, FIG. 4). Thus, a medical image data processor may be implemented by virtue of having software, firmware, hardware, or a combination of them installed on processor 122 of mobile device 120, for example, as computer-readable code performing the described color inversion process.

Referring to FIG. 5, in one aspect, Color Inversion Process 407 (FIG. 4) is used for digital image transformation of medical image data 505 (here, patient stool video frame 406). In this aspect, color inversion filter 500 includes the "Core Image" framework provided by Apple Computer, Inc., which may be used, together with a predefined color inversion filter. See e.g. https://developer.apple.com/documentation/coreimage; and https://developer.apple.com/library/archive/documentation/GraphicsImaging/Reference/CoreImageFilterReference/index.html#//app le_ref/doc/filter/ci/CIColorInvert. In this aspect, processing medical data images comprises applying image filters. For example, an image filter is a piece of software that examines an input image, pixel-by-pixel, and algorithmically applies some effect in order to create an output image. In Core Image, for example, image processing relies on "CIFilter" and "CIImage" classes, which describe filters and their input and output. See e.g. https://developer.apple.com/documentation/coreimage/cifilter and https://developer.apple.com/documentation/coreimage/ciimage. As shown in FIG. 5, Core Image filters 510 ("CISampler) and 515 ("CIKernal") process Core Image images 505 and produce Core Image images 520. A CIImage instance is an immutable object representing an image. These objects may not directly represent image bitmap data—instead, a CIImage object is a "recipe" for producing an image. Core Image performs these recipes only when the system requests that an image be rendered for display or output. This implementation is but one example of how a color-edited image 276 (FIG. 2) may be obtained in the method and system described herein. Other automated color-inversion processes may be used.

In one aspect, implementation of the automated color inversion process 407 involves applying a predefined color inversion filter from the Core Image framework, by means of applying a "CIColorMatrix" filter, which multiplies source color values and adds a bias factor to each color component See e.g. https://developer.apple.com/library/archive/documentation/Graphicsimaging/Reference/CorelmageFilterReference/index.html#//apple ref/doc/filter/ci/CIColorMatrix. For example, color inversion process 407 can create a color-edited image, susceptible to patient annotations, using the following vectors:

```
inputRVector=(-1 0 0 0)
inputGVector=(0 -1 0 0)
inputBVector=(0 0 -1 0)
inputAVector=(0 0 0 1)
inputBiasVector=(1 1 1 0)
// get CIFilter instance and CIImage representation of camera image
(video
frame)
let colorInvertFilter = CIFilter(name: "CIColorInvert")
let pixelBuffer = CMSampleBufferGetImageBuffer(sampleBuffer)
let cameraImage = CIImage(cvImageBuffer: pixelBuffer!)
// apply filter on camera image
colorInvertFilter!.setValue(cameraImage, forKey: kCIInputImageKey)
// render filtered image (image with inverted colors)
let filteredImage = UIImage(ciImage: colorInvertFilter!.value(forKey:
kCIOutputImageKey) as! CIImage)
```

Other embodiments of this aspect include corresponding devices, processing systems, and computer programs recorded on one or more computer storage devices, each configured to perform the actions of the methods described.

Figure 6:
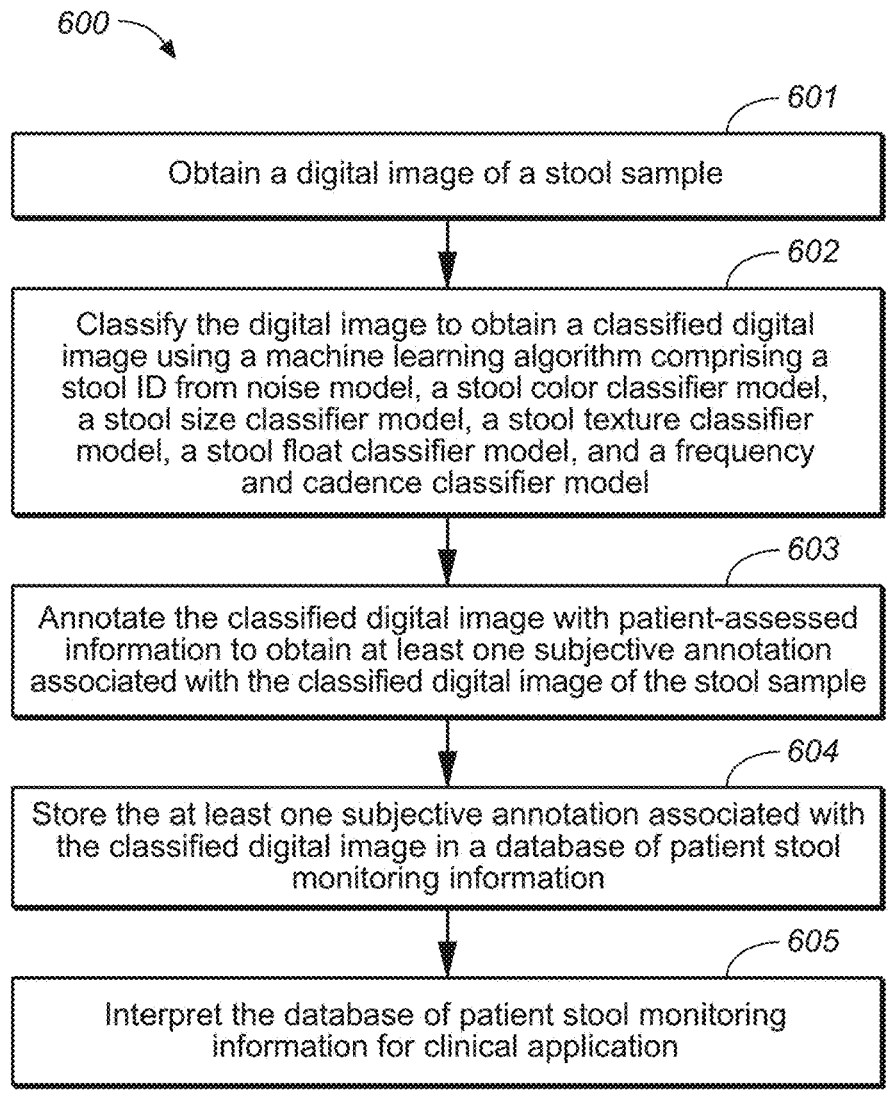
FIG. 6 is a flowchart of one aspect of the method and system described herein.

FIG. 6 is a flowchart of another aspect of the method and system described herein. In this other general aspect, a method of long-term monitoring of patient gastrointestinal function for clinical application comprises: obtaining a digital image of a stool sample (step 601), and then classifying the digital image to obtain a classified digital image using at least one machine learning algorithm (step 602). Machine learning algorithms may include, for example (as further described below): a stool ID from noise model; a stool color classifier model; stool size classifier model; a stool texture classifier model; a stool float classifier model; and a frequency and cadence classifier model. In this aspect, the method of long-term monitoring of patient gastrointestinal function also includes annotating the classified digital image with patient-assessed information (step 603), to obtain at least one subjective annotation (for example, pain and/or urgency) associated with the classified digital image of the stool sample. The method of long-term monitoring of patient gastrointestinal function also includes storing the subjective annotation(s) associated with the classified digital image in a database of patient stool monitoring information (step 604). In this aspect, the method of long-term monitoring of patient gastrointestinal function also includes interpreting the database of patient stool monitoring information for clinical application (step 605). Other embodiments of this aspect include corresponding computer systems, apparatus, devices, and computer programs recorded on one or more computer storage devices, each configured to perform actions of the methods described herein.

Referring to FIG. 6, in one aspect of the method, use of the BSS method may be used to obtain a classified digital image using a machine learning algorithm comprising the following machine-learning classifiers (step 602): stool ID from noise model; stool color classifier model; stool size classifier model; stool texture classifier model; and stool float classifier model. In addition, a frequency and cadence classifier model may also be used.

Figure 7:
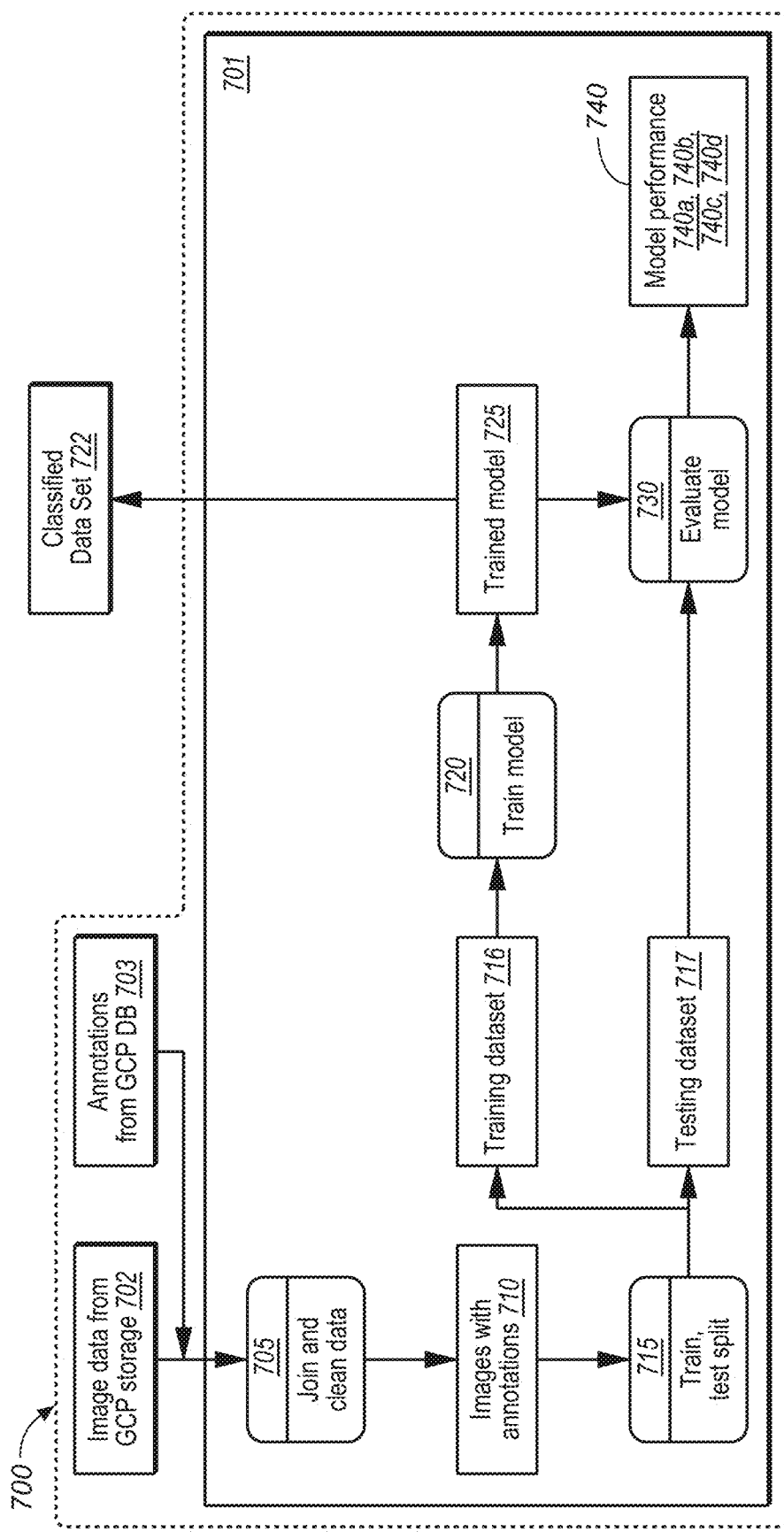
FIG. 7 is a data analysis flow diagram for a training model for one aspect of the method and system described herein.

FIG. 7 is a data analysis flow diagram describing a process for training a classification model for one aspect of the method and system described herein. In this aspect, the data analysis flow diagram for training a classification model 700 by a signal processing tool 701 (for example, by machine learning) may be explained as follows:

1. Image data 702 from remote server 320 (GCP storage). Image data 702 comprise one or more digital images of stool saved in, for example, cloud-based storage. See also FIG. 3 and descriptions of general aspects of remote server 320, database 325, and remote server memory 326 operable to store digital image 272 uploaded from mobile device 120 to remote server 320 over communication link 341.
2. Annotations 703 from server database 330. Annotations 703 comprise patient-assessed information stored in the form of annotations—for example, annotations on shape (281), color (283), size (285), float (287), urgency (289) and pain (290) of a stool event (e.g., stool event 271)—entered, for example, at the time (e.g., time 267) of the stool event (e.g., 271) by the patient and/or caregiver and associated with digital images (e.g., 272), and stored as clinical data sets 316 in server database 330 (e.g. "PostGresDB") and/or remote storage device 326 (e.g., GCP cloud-based storage). See FIG. 3.
3. Join And Clean Data Process 705. This is a process that connects annotations 703 to associated medical digital image 702 (i.e., patient stool digital images). The Join and Clean Data Process 705 removes obvious outliers, such as digital images with insignificant discernable content, annotations unassociated with a digital image, etc. This process creates at least one set of clinical data 316 for which the set of annotations 300 are associated with medical digital image 702.
4. Train, Test Split Process 715. This is a process that splits clinical data 316 into two datasets: one to train classification model 700 (training dataset 716) and one to test classification model 700 (testing dataset 717), allowing for evaluation of the classification model.
5. Train Model Process 720. This is a process training classification model 700 to obtain one or more classified clinical datasets 722. A convolutional neural network (CNN) with multiple outputs (for example, color, shape, size, float, pain, urgency) may be used. The specific CNN method used may depend upon the specific application of the system described herein.
6. Trained Model 725. This is the output from Train Model Process 720, saved in relevant format (for example, ONNX).
7. Evaluate Model Process 730. This is a process that evaluates Trained Model 725 on testing dataset 717, and outputs relevant metrics 732 for evaluating Model Performance 740 of classification model 700.
8. Model Performance 740. This is a set of metrics (for example, accuracy 740*a*, precision 740*b*, recall 740*c*, mean error 740*d*) for predictive tasks (for example, prediction of color, shape, size, float, pain, urgency) relevant to the one or more classified clinical datasets 722 and to clinical diagnostic use of the method and system.

Figure 8:
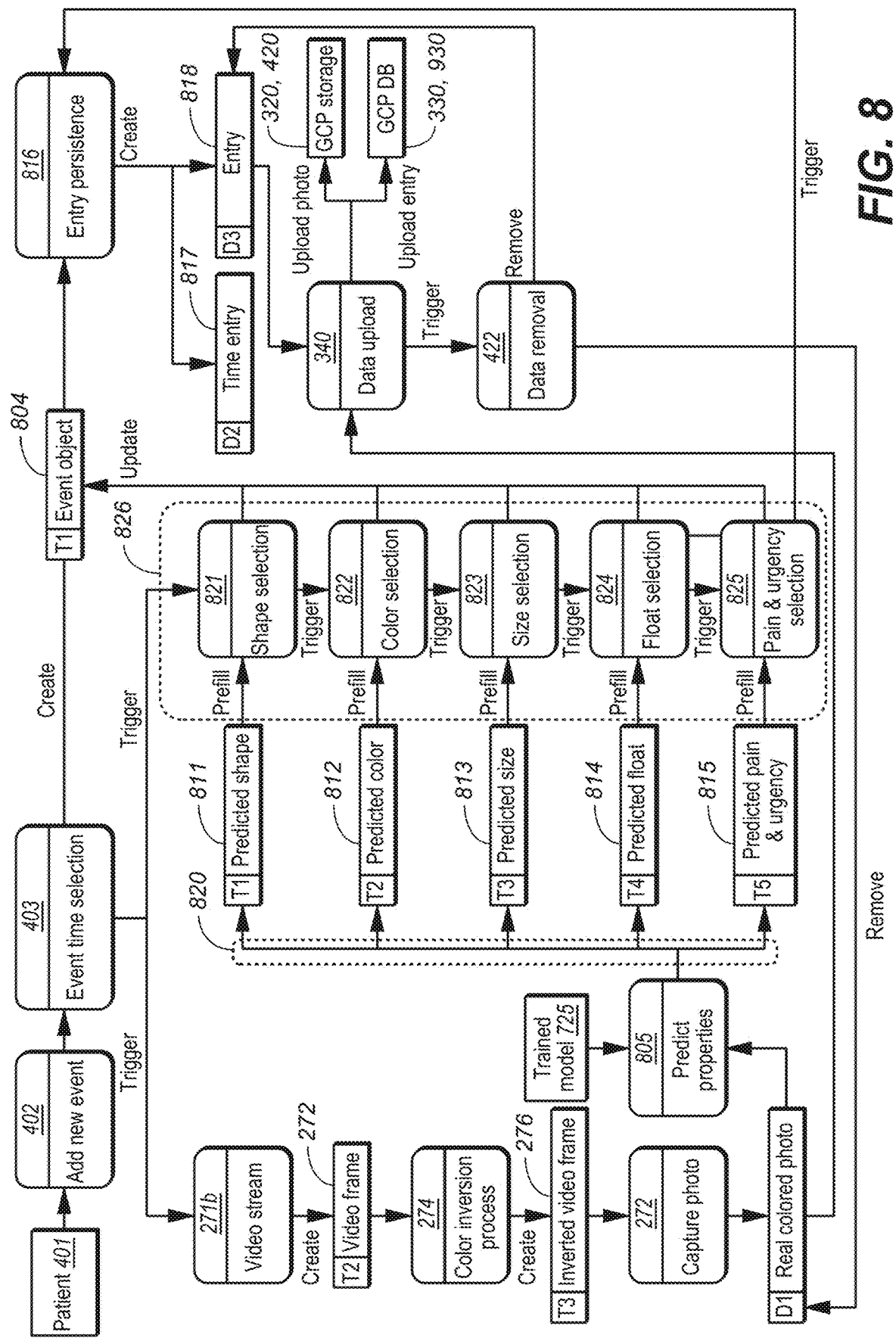
FIG. 8 is a data analysis flow diagram with trained model for one aspect of the method and system described herein.

FIG. 8 is a data analysis flow diagram with trained model for one aspect of the method described herein. In this aspect of the method and system, the flow diagram of FIG. 8 adds a machine learning algorithm component to the system of FIG. 3, which may be explained as follows:

1. Trained Model 725. This is the output of training model process as depicted in FIG. 7.
2. Predict Properties Process 805. For a given medical digital image (i.e. digital image 272), Predict Properties Process 805 is a process that predicts stool scale classifications (e.g. BSS shape 811, color 812, size 813, float 814) and subjective annotations (e.g. pain and urgency 815), to obtain predicted patient stool monitoring information 810.
3. Prefill Process 820. This is a process by which the system prefills one or more predicted stool scale classifications 820 associated with digital image 272, and allows the patient (and/or caregiver) to verify or change the prefilled stool monitoring information 826 to be included in the patient's clinical datasets 316 (see FIG. 3) for clinical application.

Other embodiments of this aspect include corresponding computer systems, apparatus, devices, and computer programs recorded on one or more computer storage devices, each configured to perform actions of the methods described herein.

Figure 9A:
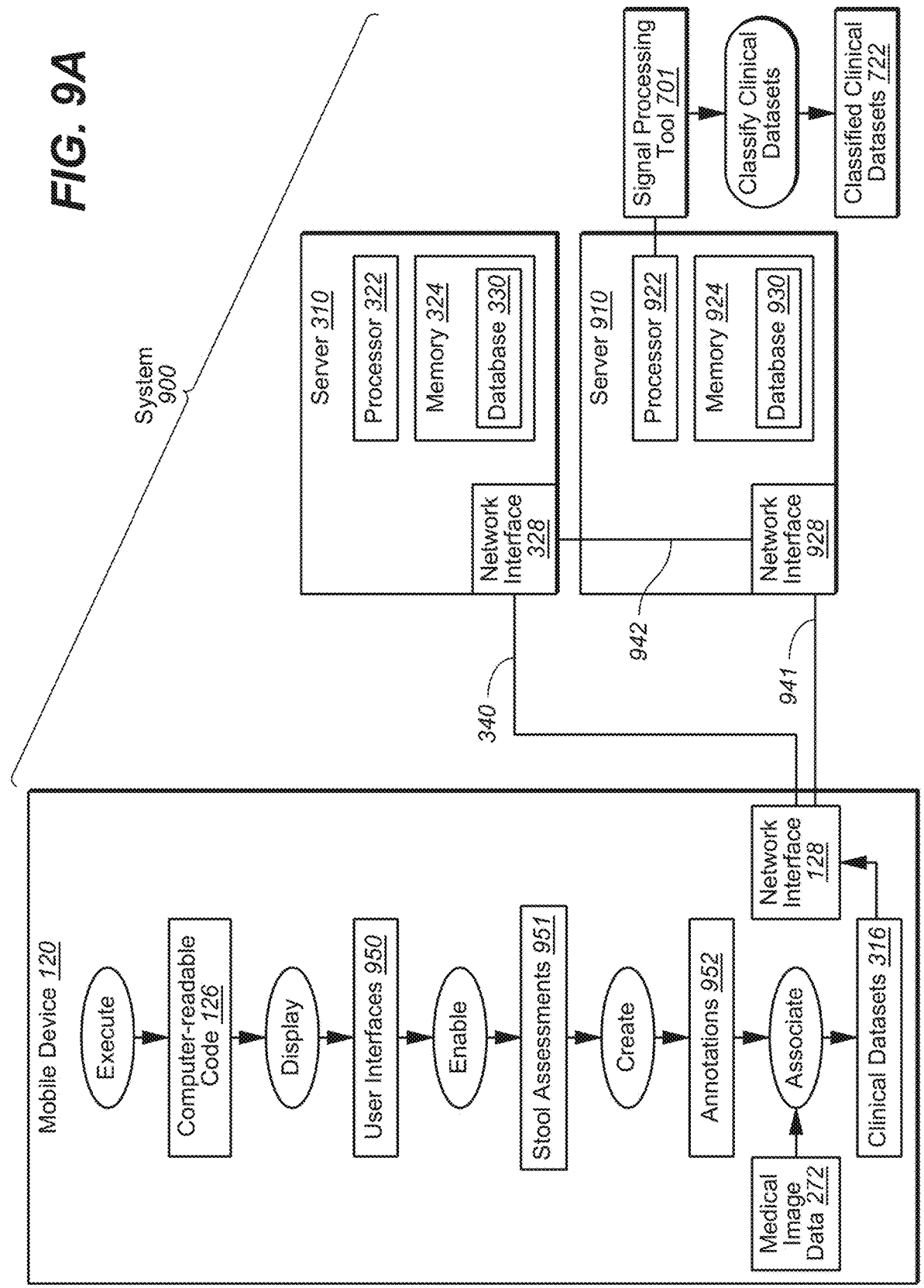

Thus, as described herein and depicted in FIG. 1B, FIGS. 2A-2T, FIG. 3, FIG. 4, FIG. 5, FIG. 7, and FIG. 8, one general aspect of the system is summarized in FIG. 9A, which shows a general schematic of a system 900 for real-time monitoring of gastrointestinal function for clinical application. System 900 includes a mobile computing device 120 (FIG. 1B) where mobile computing device 120 is programmed (via computer-readable code 126 stored in memory 124) to: (a) capture medical image data 272 relating to a patient stool (see e.g. FIG. 2O); (b) process the medical image data 272 to create a color-edited image 276 of a stool sample (see e.g. FIG. 2O); and (c) provide (e.g. display) a set of user interfaces 950 (see e.g. FIGS. 2A-2N, FIGS. 2P-2T) to enable user-entry of a set (i.e., at least one) of stool assessments 951 (see e.g. FIGS. 2A-2N, FIGS. 2P-2T), to create a set of annotations 952 to the medical image data 272, using the color-edited image 276. The color-edited image 276 may be created by an automated color-inversion process 274*a* (see FIG. 2O). When executing on the mobile computing device 120, computer-readable code 126 further causes mobile computing device 120 to store the set of annotations 952, associated with medical image data 372, in a local storage 123 of memory 124, and/or via data uploads over one or more communication links (e.g., 340 and 341; FIG. 3) to one or more remote servers (e.g., 310, 320; FIG. 3), so as to enable creation of at least one set of clinical data 316 associated with the medical image data 272. System 900 also includes server 310 that includes processor 322, memory 324 and network interface 328 (see also FIG. 3). Memory 324 is operable to store the at least one set of clinical data 316 in a database 330 (see also FIG. 3). System 900 also includes communication link 340 enabling data transfers (uploading and downloading) between the mobile device 120 and server 310, where mobile device 120 is further programmed to enable uploading over communication link 340 of the at least one set of clinical data 316 to server 310. System 900 may further comprise a server 910 comprising: a processor 922 programmed to execute signal processing tool 701, which is operable to classify the at least one set of clinical data 316 into a classified clinical dataset 722 (FIG. 7 and FIG. 8); a second memory 924 operable to store the classified clinical dataset 722 in a second database 930; and a network interface 928 enabling data transfers between server 310 and server 910 over a communication link 942.

Other embodiments of this aspect include corresponding computer systems, apparatus, and computer programs recorded on one or more computer storage devices, each configured to perform actions of the methods described herein. Implementations may include a process where the color-edited image is created by an automated color-inversion process.

FIG. 9B also shows additional optional features of one aspect of the system 900. In this aspect, a remote server 920, including a processor 922b, a memory 924b and a network interface 928b, may be configured to interpret a set of classified clinical datasets 722 (FIG. 7) using a clinical diagnostic tree 972, which is stored in a data structure 970 residing in memory 924b of remote server 920. Remote server 920 may further include a third database 932 residing, for example, in memory 924b, which stores a set of adverse clinical events 934. In this aspect, clinical diagnostic tree 972 is implemented in data structure 970; the clinical diagnostic tree 972 comprises a set of individual diagnostic heuristics 974, and a set of clinical decision making rules 976, via corresponding computer systems, apparatus, and computer programs recorded on one or more computer storage devices.

More particularly, the set of individual diagnostic heuristics 974 and clinical decision making rules 976 of clinical diagnostic tree 972 are configured to build up a process of disease and/or condition identification (i.e. what disease), and disease and/or condition progression (i.e. how severe, in what stage the condition is). This information is represented as clinical diagnostic tree 972, and is described for relevant gastroenterological diseases and conditions that system 900 can detect.

Thus, in one aspect, the set of adverse clinical events 934 are stored in third database 932 and structured by (i) condition or disease, (ii) treatment, and (iii) clinical adverse event typology. Expected and/or requested immediate clinical interventions are associated with all stored adverse event type-disease-treatment trichotomies.

Referring to FIG. 9B, data from the one or more clinical datasets 316, information 978 obtained from using clinical diagnostic tree 972, and information stored in third database 932 of adverse clinical events 934, are all processed to metadata 980. A data interpretation aspect of the system and method described herein includes computer-readable code 926, executing on processor 922b and configured to interpret a classified clinical dataset 722 using clinical diagnostic tree 972 and third database 932. In this aspect, an output of this data interpretation layer is represented by patient information 990 about, for example, (i) current clinical status of a patient—i.e., patient's diagnosis, stage, progression rate, experienced clinical adverse events, and (ii) suggestions of required immediate medical intervention or changes to continuous treatment. Metadata 980 and patient information 990 may then be used for clinical application and, for example, via a data visualization engine.

Other embodiments of this aspect include corresponding computer systems, apparatus, and computer programs recorded on one or more computer storage devices, each configured to perform actions of methods described herein. For example, FIG. 10A illustrates an example of relationships between mobile device 120 and servers 310, 910, and 920, which are described above (and collectively depicted in FIGS. 1B, 3, 9A and 9B, respectively) as individual components of system 900 interconnected via a network 1010. In general, however, any number of mobile devices and servers may be included—for example, the functionality of servers 310, 910 and 920 may be performed by one or more servers.

Figure 10B:
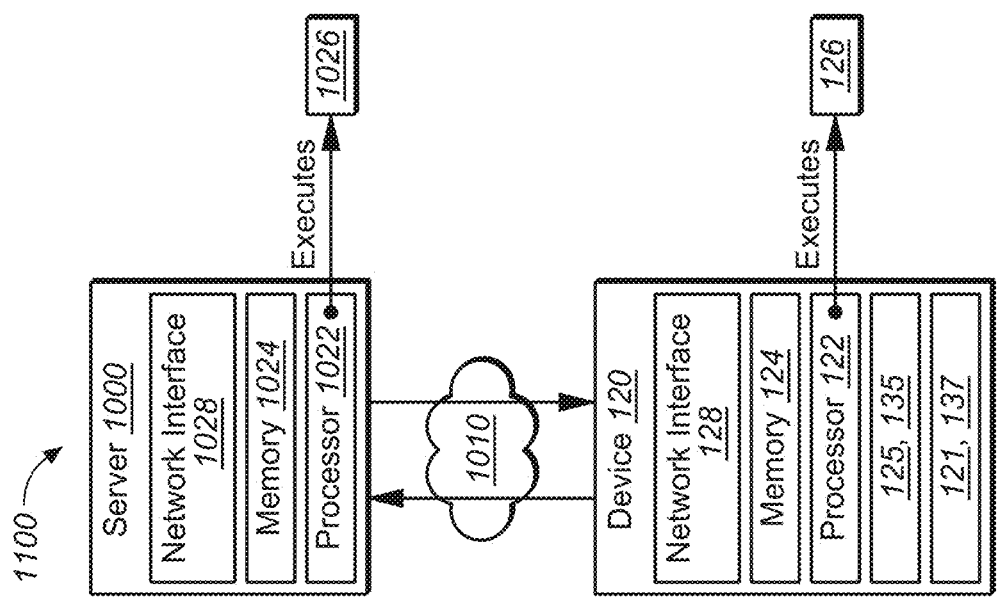
FIGS. 10A and 10B are schematics illustrating one aspect of the method and system described herein.
Figure 10A:
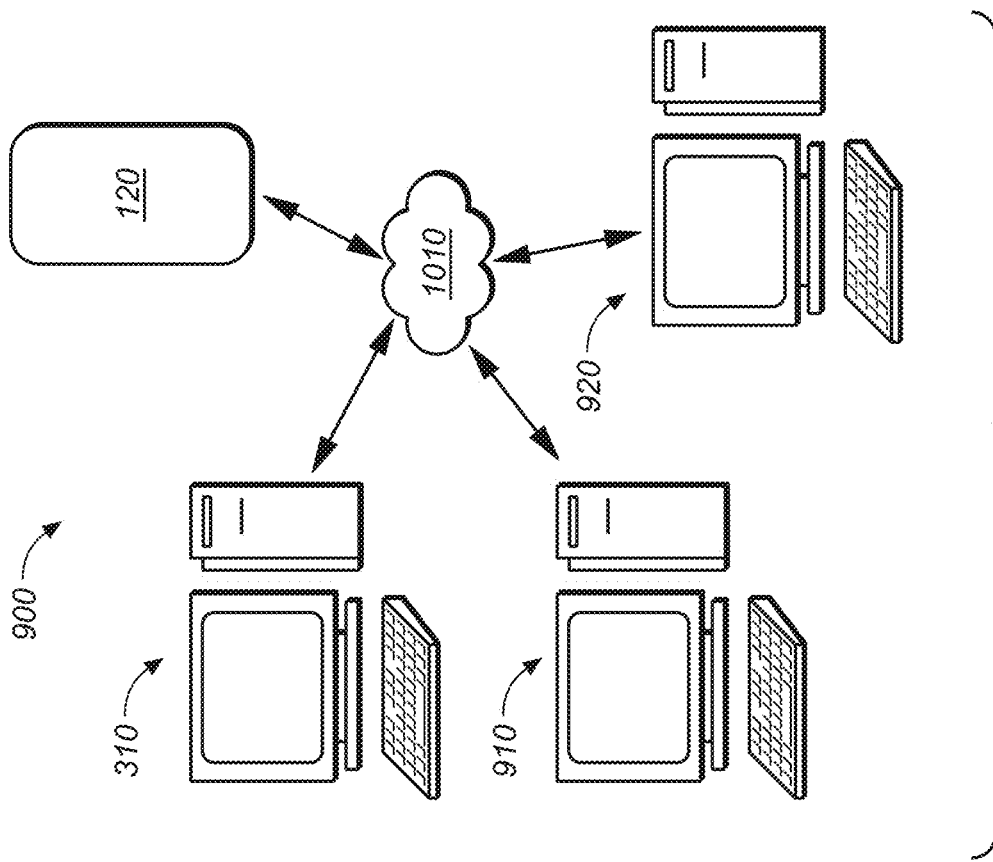

FIG. 10B further illustrates one aspect of a system programmed to perform the methods described herein. Referring to FIG. 10B, a system 1100 includes, generally, a server 1000, which itself may include programming instructions for (among other things) uploading, processing, storing and interpreting data and information collected and processed by mobile device 120, over network 1010, to provide one or more of the functionalities of the system and methods described herein. Network 1010 includes wireless communications between server 1000 and mobile device 120. In general, server 1000 may produce programming instructions, files, data or metadata that may be transmitted over network 1010 to operate mobile device 120 and/or any number of other servers in system 1100, in order to provide one or more of the functionalities as described herein. In addition, network 1010 may also provide access to interpretive information that can be retrieved and displayed on mobile device 120 and/or other devices or servers in system 1100.

In general, mobile device 120 may communicate over network 1010 to server 1000 and may include programming—in the form of computer-readable code 1026—to receive and transmit information from and to other devices in the system, as well as programming to process and store that information both locally and out-of-device, so as to provide one or more functionalities as described herein.

Server 1000 is a computer, a computer system, or network of computers or systems that may include a processor 1022, a memory 1024, and a network interface 1028. It is to be understood that processor 1022, memory 1024, and network interface 1028 are configured such that a program in the form of computer-readable code 1026 stored in the memory 1024 may be executed by the processor 1022 to accept input and/or provide output through network interface 1028 over network 1010 from and to mobile device 120, and potentially other servers and devices in the system.

Thus, as detailed in the preceding discussion above, aspects of system 1100 to perform the methods described herein are embodied and performed by server 1000 and mobile device 120, which include programs stored in memory 1024 and 124, respectively, operable to instruct processors 1022 and 122, respectively, to communicate over the network 1010, including retrieving data and information stored in memory 1024 and 124, process that data and information, and provide output on displays, such as display 135.

The method and system described herein improves upon existing and previously described methods and systems for patient-reported stool assessments. Some of the problems overcome by the method and system described herein include, among others:

1. Weak objectivity of subjective patient-reported-outcome (PRO) scales (e.g. BSS);
2. Lack of real life clinical data in stool assessment—due to an elaborate data collection process (e.g., via paper-based methods), clinical research and diagnostic efforts are restricted in terms of sample size;
3. Lack of real-time stool assessments, leading to late detection of acute complications (e.g. blood in stool), which can result in lifelong consequences or death; and
4. Lack of continual stool assessments, which restricts ability to monitor stool quality and to detect adverse events in a timely manner.

The method and system described herein also improves upon existing and previously described methods and systems for patient-reported stool assessments, by allowing and facilitating seamless data collection and automatic data analysis, and by enabling long-term, standardized, and more precise data collection for a variety of clinical applications. Furthermore, the real-time, automatic data analysis, included in the method and system described herein, enables rapid communication of detected adverse events and potentially acute patient issues to a responsible party.

Automated classification of stool type by color, texture, consistency, float, and size, and associating those classifications with subjective assessments such as pain and urgency as described herein, enables rapid visualization of all analyzed data on a timeline, for example, so as to derive frequency of a patient's various bowel movements. This aspect further enables patients, researchers and clinicians to, for example:

1. Map bowel movements in a patient profile to a basic gastroenterological diagnostic tree, and to note physiological changes associated with relapse and/or warning signs in gastrointestinal (GI) diseases;
2. Analyze in-patient "delta" and "between-cohorts" differences;
3. Add contextual value to other clinical measures, such as electronic PROs, medical history, socio-demographics, quality of life (mood, depression, stress, fatigue), and BMI; and
4. Monitor dosing (in)tolerability effects, for drugs with assumed interaction with GI system and functions.

The classification models derived from the method and system described herein may furthermore be used in (but not only restricted to) diagnostic efforts in following disease areas such as Crohn's disease, ulcerative colitis, irritable bowel syndrome, inflammatory bowel disease, endometriosis, and colon cancer.

The method and system described herein additionally allows for development of image-processing-based stool classification models, which would eliminate some or all of the following problems associated with monitoring adverse GI events and intolerability of drug dosing during human clinical trial phases of drug development (i.e. outside of clinical diagnostic process):

1. Lack of real life, real-time continual assessment of dosing effects and (in)tolerability, using instead sequential reporting (e.g. PRO once every 24 hours, or after an adverse event or status change);
2. Shortened pre- and post-trial monitoring phase—patients in human clinical trials who are not monitored continuously and/or in the long-term (as, for example, in longitudinal studies), and thus their GI performance profiles (benchmark for drug tolerability assessment) are not well-defined; and
3. In new drug or therapy development, including in human clinical trials, the onset and washout phases of any adverse event may not be assessed properly, due to the inability of real-time data analysis (i.e. real-time early onset of an adverse event and its early detection) and a lack of data in general (i.e. inability to continuously collect and analyze patient data).

The above-listed problems are addressed by the method and system described herein, because, at the very least: (a) image-processing-based classification models introduce higher precision and enable continuity of data analysis; and (b) image-processing-based classification models collect higher quality data of individual stool events, more often, thus leading to improved clinical analysis of the data.

One embodiment of methods described herein is in the form of computer-readable code that executes on a processing system, e.g., a one or more processors or computing devices that are part of a system enabling patient monitoring of gastrointestinal function using automated stool classifications. Thus, as will be appreciated by those skilled in the art, embodiments of the present invention may be embodied as a method, an apparatus such as a special purpose apparatus, an apparatus such as a data processing system, or a carrier medium, e.g., a computer program product. The carrier medium carries one or more computer-readable code segments for controlling a processing system to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code segments embodied in the medium. Any suitable computer-readable medium may be used, including a memory of a computing device, an external memory device, a solid state memory device, a flash drive, a microchip, a magnetic storage device such as a diskette or a hard disk, or an optical storage device such as a CD-ROM.

It will be understood that the steps of methods discussed are performed in one embodiment by an appropriate processor (or processors) of a processing (i.e., computer) system executing instructions (code segments) stored in storage. It will also be understood that the system and methods described herein is not limited to any particular implementation or programming technique, and may be implemented using any appropriate techniques for implementing the functionality described herein. The system and methods described herein are not limited to any particular programming language or operating system.

Reference throughout this specification to "one aspect" or "an embodiment" means that a particular feature, structure or characteristic described in connection with the aspect or embodiment is included in at least one embodiment of the system or method described herein. Thus, appearances of the phrases "in one aspect" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments. In addition, the terms "clinical data", "clinical datasets," "clinical applications" (and the like) are intended to refer generally to health-status data, datasets and applications that may be used in non-clinical settings, where the health-monitoring value of such data, datasets and applications is determined by the context of use of the system and/or method described herein, which may be non-clinical.

Similarly, it should be appreciated that in the above description of exemplary embodiments of the system and methods described herein, various features described are sometimes grouped together in a single embodiment, figure, or description thereof, for the purpose of streamlining the disclosure and aiding in the understanding of one or more of the various inventive aspects. This method of disclosure, however, is not to be interpreted as reflecting an intention that a claimed invention requires more features than are expressly recited in a claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

It should further be appreciated that although the coding of computerized methods described herein has not been discussed in detail, the invention is not limited to a specific coding method. Furthermore, the system is not limited to any one type of network architecture and method of encapsulation, and thus may be utilized in conjunction with one or a combination of other network architectures/protocols.

Finally, those skilled in the art will recognize that other and further modifications may be made thereto without departing from the spirit of the system and methods described herein, and it is intended to claim all such changes and modifications as fall within the scope of the invention. For example, any specific formulas, pseudo-code, data structures, system architectures, process flows, data analysis flows, graphical user interfaces, etc., described herein are merely representative of what may be used. Functionality may be added or deleted from the block diagrams and operations may be interchanged among functional blocks. Steps may be added or deleted to methods described within the scope of the present invention.

We claim:

1. A method of facilitating data collection of stool data associated with a digital image of a stool sample, where the digital image is captured by a mobile device comprising a camera, a processor, and memory, the method comprising:
   providing computer-readable code to the mobile device which, when executing on the mobile device,
      enables automated editing of color in the digital image to create a color-edited image,
      enables user-entry of at least one stool assessment to create at least one annotation associated with the digital image using the color-edited image, and
      enables the mobile device to store the at least one annotation in the memory.

2. The method of claim 1, wherein the color-edited image is created using an automated color-inversion process.

3. The method of claim 2, wherein at least one annotation is associated with the digital image in real-time.

4. The method of claim 1, wherein the at least one annotation comprises at least one subjective annotation associated with the stool sample.

5. The method of claim 4, further comprising uploading the at least one annotation to a patient database so as to enable patient monitoring of gastrointestinal function over time.

6. The method of claim 1, wherein the at least one annotation comprises a stool scale classification.

7. The method of claim 6, wherein the stool scale classification is based on a Bristol Stool Chart.

8. The method of claim 1, further comprising providing computer-readable code to the mobile device which, when executing on the mobile device, enables the mobile device to upload the digital image to a server.

9. The method of claim 8, wherein the server comprises a cloud-based storage.

10. A computerized method of long-term monitoring of patient gastrointestinal function, the computerized method comprising:
    obtaining a digital image of a stool sample;
    classifying the digital image, using a signal processing tool, to obtain a classified digital image;
    annotating the classified digital image with patient-assessed information, to obtain at least one subjective annotation associated with the classified digital image of the stool sample;
    storing the at least one subjective annotation associated with the classified digital image in a database of stool monitoring information; and
    interpreting the database of stool monitoring information.

11. The method of claim 10, wherein the signal processing tool includes a machine learning algorithm comprising a stool ID from noise model.

12. The method of claim 10, wherein the signal processing tool includes a machine learning algorithm comprising a stool color classifier model.

13. The method of claim 10, wherein the signal processing tool includes a machine learning algorithm comprising a stool size classifier model.

14. The method of claim 10, wherein the signal processing tool includes a machine learning algorithm comprising a stool texture classifier model.

15. The method of claim 10, wherein the signal processing tool includes a machine learning algorithm comprising a stool float classifier model.

16. The method of claim 10, wherein the signal processing tool includes a machine learning algorithm comprising a frequency and cadence classifier model.

17. A system for real-time monitoring of gastrointestinal function for clinical application, the system comprising:
    a mobile device comprising a camera, a processor, and device memory, wherein the mobile device is programmed to capture medical image data relating to a patient stool,
       process the medical image data to create a color-edited image,
       provide a user interface to enable entry of at least one stool assessment to create at least one annotation to the medical image data using the color-edited image, and
       store the at least one annotation and the medical image data, so as to enable creation of at least one set of clinical data associated with the medical image data;
    a server comprising server memory operable to store the at least one set of clinical data in a database; and
    a communication link between the mobile device and the server, wherein the mobile device is further programmed to enable uploading over the communication link the at least one set of clinical data from the mobile device to the server.

18. The system of claim 17, wherein the color-edited image is created by an automated color-inversion process.

19. The system of claim 17, wherein the server further comprises a server processor, wherein the server processor is programmed to
    execute a signal processing tool operable to classify the at least one set of clinical data into a classified clinical dataset, and
    store the classified clinical dataset in a second database in the server memory.

20. The system of claim 19, further comprising:
    a data structure comprising a clinical diagnostic tree stored in the server memory, and
    a plurality of adverse clinical events stored in a third database in the server memory, and
    wherein the server processor is further programmed to interpret the classified clinical dataset using the clinical diagnostic tree and the third database.

21. The system of claim 20, wherein said server comprises a first server comprising a first processor and a first server memory, a second server comprising a second server processor and a second server memory, and a third server comprising a third server processor and a third server memory, wherein
    the at least one set of clinical data is stored in the first server memory,
    the second database is stored in the second server memory,
    the clinical diagnostic tree is stored in the third server memory, and the third database is stored in the third server memory.

22. A computer program product comprising:
A memory including computer-readable code stored therein,
wherein the computer-readable code, when executed on a mobile computing device,
causes the mobile computing device to
create a digital image of a stool sample,
edit color in the digital image using an automated color-inversion process to create a color-edited image,
create a set of annotations associated with the digital image and the color-edited image, and
store the set of annotations in a memory of the mobile computing device.

23. The computer program product of claim 22, wherein the computer-readable code further causes the mobile computing device to upload the set of annotations to a storage device.

24. The computer program product of claim 23, wherein the computer-readable code further causes the mobile computing device to upload the digital image to a second storage device.

\* \* \* \* \*